US009448176B2

(12) United States Patent
Matsuno et al.

(10) Patent No.: US 9,448,176 B2
(45) Date of Patent: Sep. 20, 2016

(54) VARIABLE WAVELENGTH INTERFERENCE FILTER, OPTICAL FILTER DEVICE, OPTICAL MODULE, AND ELECTRONIC APPARATUS

(75) Inventors: Yasushi Matsuno, Matsumoto (JP); Akira Sano, Shiojiri (JP)

(73) Assignee: Seiko Epson Corporation (JP)

( * ) Notice: Subject to any disclaimer, the term of this patent is extended or adjusted under 35 U.S.C. 154(b) by 577 days.

(21) Appl. No.: 13/602,885

(22) Filed: Sep. 4, 2012

(65) Prior Publication Data

US 2013/0083398 A1  Apr. 4, 2013

(30) Foreign Application Priority Data

Sep. 29, 2011 (JP) ................. 2011-214876

(51) Int. Cl.
*G01J 3/50* (2006.01)
*G01J 3/26* (2006.01)
*G02B 26/00* (2006.01)
*G01N 21/65* (2006.01)

(52) U.S. Cl.
CPC .............. *G01N 21/658* (2013.01); *G01J 3/26* (2013.01); *G01J 3/502* (2013.01); *G02B 26/001* (2013.01)

(58) Field of Classification Search
CPC G02B 26/001; G02B 5/284; G02B 6/29358; G01J 3/26; G01J 3/502; G01N 21/658
USPC .......... 359/260–261, 577–590; 356/450–521
See application file for complete search history.

(56) References Cited

U.S. PATENT DOCUMENTS

| 7,246,980 | B2 | 7/2007 | Azzalin et al. |
| 7,370,185 | B2 | 5/2008 | Piehl et al. |
| 7,447,891 | B2 | 11/2008 | Faase et al. |
| 2005/0057331 | A1* | 3/2005 | Murata ........................... 335/78 |
| 2007/0158826 | A1* | 7/2007 | Sakakibara et al. .......... 257/723 |
| 2007/0242920 | A1* | 10/2007 | Lin et al. ........................ 385/27 |
| 2009/0103166 | A1* | 4/2009 | Khazeni ............... G02B 26/001 359/290 |

FOREIGN PATENT DOCUMENTS

| JP | 01-313722 | 12/1989 |
| JP | 02-257676 | 10/1990 |
| JP | 07-243963 | 9/1995 |

(Continued)

*Primary Examiner* — Kimberly N Kakalec
(74) *Attorney, Agent, or Firm* — Harness, Dickey & Pierce, P.L.C.

(57) ABSTRACT

A variable wavelength interference filter includes a stationary substrate, a movable substrate bonded to the stationary substrate, a stationary reflecting film provided to the stationary substrate, a movable reflecting film provided to the movable substrate, and opposed to the stationary reflecting film across an inter-reflecting film gap, and an electrostatic actuator adapted to vary the gap amount of the inter-reflecting film gap by deflecting the movable substrate toward the stationary substrate, a releasing space to which air between the stationary reflecting film and the movable reflecting film moves when the gap amount of the inter-reflecting film gap is reduced is provided between the stationary substrate and the movable substrate, and assuming that a spring constant of the movable substrate is $k_v$, and a spring constant of the air existing in the inter-reflecting film gap is $k_{air}$, $k_v \geq 20 \times k_{air}$ is satisfied.

11 Claims, 14 Drawing Sheets

(56) References Cited

FOREIGN PATENT DOCUMENTS

| | | |
|---|---|---|
| JP | 10-511772 A | 11/1998 |
| JP | 2000-266605 | 9/2000 |
| JP | 2005-062380 | 3/2005 |
| JP | 2005-309174 A | 11/2005 |
| JP | 2006-525554 | 11/2006 |
| JP | 2008-241738 | 10/2008 |
| JP | 2009-131911 | 6/2009 |
| JP | 2011-112998 A | 6/2011 |
| WO | WO-96-21140 A1 | 7/1996 |

* cited by examiner

VARIABLE WAVELENGTH INTERFERENCE FILTER, OPTICAL FILTER DEVICE, OPTICAL MODULE, AND ELECTRONIC APPARATUS

BACKGROUND

1. Technical Field

The present invention relates to a variable wavelength interference filter, an optical filter device, an optical module, and an electronic apparatus.

2. Related Art

In the past, there has been known a variable wavelength interference filter having reflecting films disposed on respective surfaces of a pair of substrates, the surfaces being opposed to each other, across a gap (a distance between the reflecting films) of a predetermined amount (see, e.g., JP-A-7-243963).

The optical resonator (the variable wavelength interference filter) described in JP-A-7-243963 is provided with a glass substrate having a recessed section formed on the surface thereof, and a diaphragm substrate blocking up the recessed section, and the diaphragm substrate is bonded so as to block up the recessed section of the glass substrate. Further, reflecting films opposed to each other and electrodes opposed to each other are respectively disposed on the bottom of the recessed section and the surface of the diaphragm substrate opposed to the recessed section. Further, the diaphragm substrate has a thick-wall section with a predetermined thickness and a thin-wall section thinner than the thick-wall section disposed in an area opposed to the recessed section, and by applying a voltage between the electrodes, the thin-wall section is deflected to thereby move the thick-wall section back and forth with respect to the recessed section.

Incidentally, in such a variable wavelength interference filter as described in JP-A-7-243963, there has been a problem that when displacing the thick-wall section toward the glass substrate, the air between the diaphragm substrate and the glass substrate acts as a resistance, and thus the time until the vibration of the thick-wall section stops is increased, and the response is degraded.

In contrast thereto, there has been considered a configuration of reducing the pressure of a space between the diaphragm substrate and the glass substrate to thereby reduce the air resistance (see, e.g., JP-A-2008-241738).

In the variable-shape mirror of JP-A-2008-241738, a thin mirror is housed inside a package kept in a reduced-pressure state. The variable-shape mirror is provided with a plurality of stationary electrodes opposed to the thin mirror, and by applying a voltage between each of the stationary electrodes and the thin mirror, the shape of the thin mirror is changed due to the electrostatic attractive force.

As described above, by housing the variable wavelength interference filter described in JP-A-7-243963 in the package with the reduced inside pressure described in JP-A-2008-241738, it becomes possible to improve the response in displacing the thick-wall section. However, in some cases, the time after displacing the thick-wall section and until the vibration of the thick-wall section stops to thereby make it possible to take out the light with a target wavelength is not sufficiently improved simply by driving the variable wavelength interference filter under the reduced-pressure environment.

Specifically, when applying the voltage between the electrodes of the variable wavelength interference filter described in JP-A-7-243963 to thereby displace the thick-wall section, the spring force of the thin-wall section, and the spring force (the air spring force) due to the air between the diaphragm substrate and the glass substrate act on the thick-wall section, and the vibration occurs. Here, the resistance due to the air spring is reduced by evacuating the air between the thick-wall section and the glass substrate to an outside space, and in some cases, even after the vibration of the thick-wall section stops, the air fails to completely evacuate to the outside space, and the resistance due to the air spring remains. In this case, there arises a problem that it results that the gap amount of an inter-reflecting film gap fluctuates until the resistance due to the air spring vanishes, and the time until the stable state in which the light with the target wavelength can be taken out occurs is increased.

SUMMARY

An advantage of some aspects of the invention is to provide a variable wavelength interference filter, an optical filter device, an optical module, and an electronic apparatus capable of promptly making a transition to a stable state.

A variable wavelength interference filter according to an aspect of the invention includes a first substrate, a second substrate opposed to the first substrate, and bonded to the first substrate, a first reflecting film provided to the first substrate, a second reflecting film provided to the second substrate, and opposed to the first reflecting film across an inter-reflecting film gap having a predetermined gap amount, and a gap amount changing section adapted to vary the gap amount of the inter-reflecting film gap by deflecting at least a part of the second substrate toward the first substrate, a releasing space, to which air between the first reflecting film and the second reflecting film moves when at least a part of the second substrate is deflected toward the first substrate due to the gap amount changing section, is disposed between the first substrate and the second substrate, and assuming that an air spring constant of the air between the first reflecting film and the second reflecting film is $k_{air}$, and a spring constant of the second substrate is $k_v$, the following relationship is satisfied.

$$k_v \geq 20 \times k_{air}$$

In this aspect of the invention, when the second reflecting film provided to the second substrate is displaced toward the first substrate to thereby vary the gap amount of the inter-reflecting film gap, a part of the second substrate provided with the second reflecting film vibrates due to the action of the spring force caused by the second substrate and the spring force (the air spring force) of the air spring caused by the air existing in the inter-reflecting film gap. On this occasion, the air existing in the inter-reflecting film gap escapes to the releasing space in response to a decrease in gap amount of the inter-reflecting film gap, and the action of the air spring force is reduced gradually. Then, when the air spring force to the second substrate vanishes, and the vibration stops over time, the gap amount of the inter-reflecting film gap is kept at a constant value, and the stable state in which the light with the target wavelength can stably be taken out is obtained.

Here, the inventors have newly found out that assuming that the spring constant of the second substrate is $k_v$, and the spring constant of the air spring due to the air existing in the inter-reflecting film gap is $k_{air}$, if Formula (1) below is satisfied, the time (hereinafter referred to as gap amount stabilization time) until the stable state is reached is dramatically reduced.

$$k_v \geq 20 \times k_{air} \tag{1}$$

Specifically, if Formula (1) described above is satisfied, when varying the gap amount of the inter-reflecting film gap, the air existing in the inter-reflecting film gap escapes to the releasing space before the vibration of the second reflecting film stops, or at the time when the vibration of the second reflecting film has stopped, and the air spring force stops acting on the second substrate. Therefore, the gap amount variation of the inter-reflecting film gap stops at the time when the vibration stops, and the variable wavelength interference filter comes into the stable state. Thus, it is possible to reduce the time (the gap amount stabilization time) until the gap amount variation of the inter-reflecting film gap vanishes compared to the case in which Formula (1) described above is not satisfied.

In the variable wavelength interference filter of the above aspect of the invention, it is preferable that a gap amount between the first substrate and the second substrate in the releasing space is larger than the gap amount of the inter-reflecting film gap.

In this configuration, the dimension between the first substrate and the second substrate in the releasing space is larger than the gap amount of the inter-reflecting film gap. Therefore, when decreasing the gap amount of the inter-reflecting film gap, it becomes easy for the air existing in the inter-reflecting film gap to escape to the releasing space. Thus, since it is possible to let the air existing in the inter-reflecting film gap out to the releasing space more promptly, the time until the action of the air spring vanishes is also reduced, and reduction of the gap amount stabilization time can surely be achieved.

In the variable wavelength interference filter of the above aspect of the invention, it is preferable that the second substrate includes a movable section provided with the second reflecting film, and a holding section adapted to hold the movable section so as to be able to move back and forth with respect to the first substrate.

In this configuration, the second substrate is provided with the movable section and the holding section, and by deflecting the holding section, the gap amount of the inter-reflecting film gap can be varied while keeping the shape of the movable section. Therefore, even in the case of varying the gap amount of the inter-reflecting film gap, no deflection is caused in the second reflecting film of the movable section, and the parallel relationship between the first reflecting film and the second reflecting film can be maintained. Thus, it is possible to prevent or suppress degradation in resolution of the variable wavelength interference filter.

Further, in this configuration, even in the case in which the amount of the gap between the movable section and the first substrate and the amount of the gap between the holding section and the first substrate are equal to each other, when deflecting the movable section toward the first substrate, the amount of the gap between the holding section and the first substrate becomes larger than the amount of the gap between the movable section and the first substrate. Therefore, it is possible to let the air (the air existing in the inter-reflecting film gap) existing between the movable section and the first substrate out to the releasing space on the holding section and the first substrate side, and the releasing space can be formed of the space between the holding section and the first substrate.

In the variable wavelength interference filter of the above aspect of the invention, it is preferable that the gap amount changing section includes a first electrode provided to the first substrate, and a second electrode provided to the second substrate and opposed to the first electrode across an inter-electrode gap.

In this configuration, the gap amount changing section is formed of an electrostatic actuator having the first electrode provided to the first substrate and the second electrode provided to the second substrate, and it becomes possible to accurately vary the gap amount of the inter-reflecting film gap to the desired value by applying a voltage between the first electrode and the second electrode.

A variable wavelength interference filter according to another aspect of the invention includes a substrate, a first reflecting film, a second reflecting film provided to the substrate, and opposed to the first reflecting film, and a distance changing section adapted to change a distance between the first reflecting film and the second reflecting film by deflecting the substrate, and assuming that an air spring constant of the air between the first reflecting film and the second reflecting film is $k_{air}$, and a spring constant of the substrate is $k_v$, the following relationship is satisfied.

$$k_v \geq 20 \times k_{air}$$

In this aspect of the invention, similarly to the above aspect of the invention, the air spring constant $k_{air}$ of the air between the first reflecting film and the second reflecting film and the spring constant $k_v$ of the substrate fulfill Formula (1) described above. Therefore, when deflecting the substrate, the air spring force stops acting on the substrate before the vibration of the second reflecting film stops, or at the time when the vibration of the second reflecting film has stopped. Therefore, the variation in the distance between the first reflecting film and the second reflecting film stops at the time when the vibration stops, and the variable wavelength interference filter comes into the stable state.

An optical filter device according to still another aspect of the invention includes a variable wavelength interference filter including a first substrate, a second substrate opposed to the first substrate, and bonded to the first substrate, a first reflecting film provided to the first substrate, a second reflecting film provided to the second substrate, and opposed to the first reflecting film across an inter-reflecting film gap having a predetermined gap amount, and a gap amount changing section adapted to vary the gap amount of the inter-reflecting film gap by deflecting at least a part of the second substrate toward the first substrate, wherein a releasing space, to which air between the first reflecting film and the second reflecting film moves when at least a part of the second substrate is deflected toward the first substrate due to the gap amount changing section, is disposed between the first substrate and the second substrate, and a housing adapted to house the variable wavelength interference filter, and assuming that an air spring constant of the air between the first reflecting film and the second reflecting film is $k_{air}$, and a spring constant of the second substrate is $k_v$, the following relationship is satisfied.

$$k_v \geq 20 \times k_{air}$$

In this aspect of the invention, the spring constant $k_v$ of the second substrate and the air spring constant $k_{air}$ of the air existing in the inter-reflecting film gap fulfill Formula (1) described above. Therefore, similarly to the aspects of the invention described above, when varying the gap amount of the inter-reflecting film gap, the influence of the air spring due to the air existing in the inter-reflecting film gap is reduced until the vibration of the part of the second substrate, to which the second reflecting film is provided, stops. Thus, the gap amount of the inter-reflecting film gap does not vary after the vibration stops, and it is possible to promptly set the stable state in which the light with the desired target wavelength can be taken out.

Further, since the variable wavelength interference filter is housed in the housing, it is possible to prevent the deterioration of the reflecting films due to gases or the like included in the atmosphere, and adhesion of foreign matters, and it is also possible to protect the variable wavelength interference filter from an external impact.

In the optical filter device of the above aspect of the invention, it is preferable that the variable wavelength interference filter includes a communication section adapted to make a space sandwiched between the first substrate and the second substrate, and an internal space of the housing communicate with each other, and the housing has an enclosed structure, and has internal pressure reduced to a state satisfying the following relationship.

$$k_v \geq 20 \times k_{air}$$

In this configuration, since the communication section is provided to the variable wavelength interference filter, it is possible to make the air pressure in the inter-reflecting film gap and the releasing space of the variable wavelength interference filter and the air pressure in the housing equal to each other. Further, the pressure in the housing is kept constant due to the enclosed structure, and the pressure is kept in the value satisfying Formula (1) described above.

According to such a configuration, it is possible to easily obtain a configuration satisfying Formula (1) described above by reducing the pressure in the housing, and it is also possible to reduce the drive force necessary to vary the gap amount of the inter-reflecting film gap.

In other words, in the case of driving the variable wavelength interference filter under the atmospheric pressure, in order to reduce the gap amount stabilization time, it is desirable to fulfill Formula (1) described above. In this case, it becomes possible to further increase the spring constant of the second substrate, and in order to vary the gap amount of the inter-reflecting film gap by deflecting the second substrate, stronger drive force is required. In the case of obtaining the drive force by an electrostatic actuator, extremely high electrical power is required. Further, although it is possible to reduce only the pressure in the inter-reflecting film gap and the releasing space of the variable wavelength interference filter so as to fulfill Formula (1) described above, in this case, it is necessary to seal the inter-reflecting film gap and the releasing space. Further, it is necessary to increase the strength of the second substrate, or to provide an additional reinforcing structure so that the second substrate is not deflected by the pressure outside the variable wavelength interference filter. In the case of increasing the strength of the second substrate, it is necessary to increase the drive force for deflecting the second substrate, which is disadvantageous in view of the power consumption. Further, in the case of providing an additional reinforcing structure, the configuration is complicated, the manufacturing cost grows, and the production efficiency is also degraded.

In contrast thereto, in the configuration of reducing the pressure in the housing, the configuration for reinforcing the second substrate described above can be eliminated, and the configuration satisfying Formula (1) described above can easily be realized. Further, since the spring constant of the second substrate can be reduced, the drive force for changing the gap amount of the inter-reflecting film gap can also be reduced, and in the case of, for example, varying the gap amount of the inter-reflecting film gap with electrical power, power saving can be achieved.

Further, since it is sufficient to set the pressure in the housing to the pressure satisfying Formula (1) described above, the manufacturing cost can be reduced compared to the case of, for example, making the vacuum condition, and the production efficiency is improved.

An optical filter device according to yet another aspect of the invention includes a substrate, a first reflecting film, a second reflecting film provided to the substrate, and opposed to the first reflecting film, a distance changing section adapted to change a distance between the first reflecting film and the second reflecting film by deflecting the substrate, and a housing adapted to house the substrate, the first reflecting film, the second reflecting film, and the distance changing section, and assuming that an air spring constant of the air between the first reflecting film and the second reflecting film is $k_{air}$, and a spring constant of the substrate is $k_v$, the following relationship is satisfied.

$$k_v \geq 20 \times k_{air}$$

In this aspect of the invention, similarly to the above aspects of the invention, since the air spring constant $k_{air}$ of the air between the first reflecting film and the second reflecting film and the spring constant $k_v$ of the substrate fulfill Formula (1) described above, it is possible to promptly set the stable state in which the variation in the distance between the first reflecting film and the second reflecting film vanishes. Further, since the substrate, the first reflecting film, and the second reflecting film are housed in the housing, it is possible to prevent the deterioration of the reflecting films due to gases or the like included in the atmosphere, and adhesion of foreign matters.

An optical module according to still yet another aspect of the invention includes a first substrate, a second substrate opposed to the first substrate, and bonded to the first substrate, a first reflecting film provided to the first substrate, a second reflecting film provided to the second substrate, and opposed to the first reflecting film across an inter-reflecting film gap, a gap amount changing section adapted to vary the gap amount of the inter-reflecting film gap by deflecting the second substrate toward the first substrate, and a detection section adapted to detect the light taken out by the first reflecting film and the second reflecting film, a releasing space to which air between the first reflecting film and the second reflecting film moves when the gap amount of the inter-reflecting film gap is reduced is disposed between the first substrate and the second substrate, and assuming that an air spring constant of the air between the first reflecting film and the second reflecting film is $k_{air}$, and a spring constant of the second substrate is $k_v$, the pressure of the air is set to a pressure satisfying the following relationship.

$$k_v \geq 20 \times k_{air}$$

In this aspect of the invention, similarly to the above aspects of the invention, the spring constant $k_v$ of the second substrate and the air spring constant $k_{air}$ of the air existing in the inter-reflecting film gap fulfill Formula (1) described above. Therefore, similarly to the aspects of the invention described above, when varying the gap amount of the inter-reflecting film gap, the influence of the air spring due to the air existing in the inter-reflecting film gap is reduced until the vibration of the part of the second substrate, to which the second reflecting film is provided, stops. Thus, the gap amount of the inter-reflecting film gap does not vary after the vibration stops, and it is possible to promptly set the variable wavelength interference filter to the stable state, in which the light with the desired target wavelength can be taken out.

Further, since the gap amount stabilization time is reduced, the light intensity detection by the detection section can also be performed promptly. In particular, in the case of, for example, performing the spectrum analysis of the measurement object light by sequentially varying the gap amount of the inter-reflecting film gap, speeding-up of the processing can be achieved.

An optical module according to still another aspect of the invention includes a substrate, a first reflecting film, a second reflecting film provided to the substrate, and opposed to the first reflecting film, a distance changing section adapted to change a distance between the first reflecting film and the second reflecting film by deflecting the substrate, and a detection section adapted to detect the light taken out by the first reflecting film and the second reflecting film, and assuming that an air spring constant of the air between the first reflecting film and the second reflecting film is $k_{air}$, and a spring constant of the substrate is $k_v$, the following relationship is satisfied.

$$k_v \geq 20 \times k_{air}$$

In this aspect of the invention, similarly to the above aspects of the invention, since the air spring constant $k_{air}$ of the air between the first reflecting film and the second reflecting film and the spring constant $k_v$ of the substrate fulfill Formula (1) described above, it is possible to promptly set the stable state in which the variation in the distance between the first reflecting film and the second reflecting film stops. Further, since the time until the variation in the distance between the first reflecting film and the second reflecting film vanishes is reduced, the light intensity detection by the detection section can also be performed promptly.

An electronic apparatus according to still another aspect of the invention includes a first substrate, a second substrate opposed to the first substrate, and bonded to the first substrate, a first reflecting film provided to the first substrate, a second reflecting film provided to the second substrate, and opposed to the first reflecting film across an inter-reflecting film gap, and a gap amount changing section adapted to vary the gap amount of the inter-reflecting film gap by deflecting the second substrate toward the first substrate, a releasing space to which air between the first reflecting film and the second reflecting film moves when the gap amount of the inter-reflecting film gap is reduced is disposed between the first substrate and the second substrate, and assuming that an air spring constant of the air between the first reflecting film and the second reflecting film is $k_{air}$, and a spring constant of the second substrate is $k_v$, the pressure of the air is set to a pressure satisfying the following relationship.

$$k_v \geq 20 \times k_{air}$$

In this aspect of the invention, similarly to the above aspects of the invention, the spring constant $k_v$ of the second substrate and the air spring constant $k_{air}$ of the air existing in the inter-reflecting film gap fulfill Formula (1) described above. Therefore, similarly to the aspects of the invention described above, when varying the gap amount of the inter-reflecting film gap, the influence of the air spring due to the air existing in the inter-reflecting film gap is reduced until the vibration of the part of the second substrate, to which the second reflecting film is provided, stops. Thus, it is possible to promptly set the stable state, in which the gap amount of the inter-reflecting film gap does not vary, and the light with the desired target wavelength can be taken out, after the vibration stops.

Further, since the gap amount stabilization time is reduced, speeding-up of the processing can also be achieved in each of the electronic processes performed based on the light with the target wavelength taken out by the variable wavelength interference filter.

An electronic apparatus according to yet another aspect of the invention includes a substrate, a first reflecting film, a second reflecting film provided to the substrate, and opposed to the first reflecting film, and a distance changing section adapted to change a distance between the first reflecting film and the second reflecting film by deflecting the substrate, and assuming that an air spring constant of the air between the first reflecting film and the second reflecting film is $k_{air}$, and a spring constant of the substrate is $k_v$, the following relationship is satisfied.

$$k_v \geq 20 \times k_{air}$$

In this aspect of the invention, similarly to the above aspects of the invention, since the air spring constant $k_{air}$ of the air between the first reflecting film and the second reflecting film and the spring constant $k_v$ of the substrate fulfill Formula (1) described above, it is possible to promptly set the stable state in which the variation in the distance between the first reflecting film and the second reflecting film stops. Further, since the time until the variation in the distance between the first reflecting film and the second reflecting film vanishes is reduced, speeding-up of the processing can also be achieved in each of the electronic processes performed based on the light with the target wavelength thus taken out.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention will hereinafter be explained with reference to the accompanying drawings.

1. Schematic Configuration of Colorimetric Device

Figure 1:
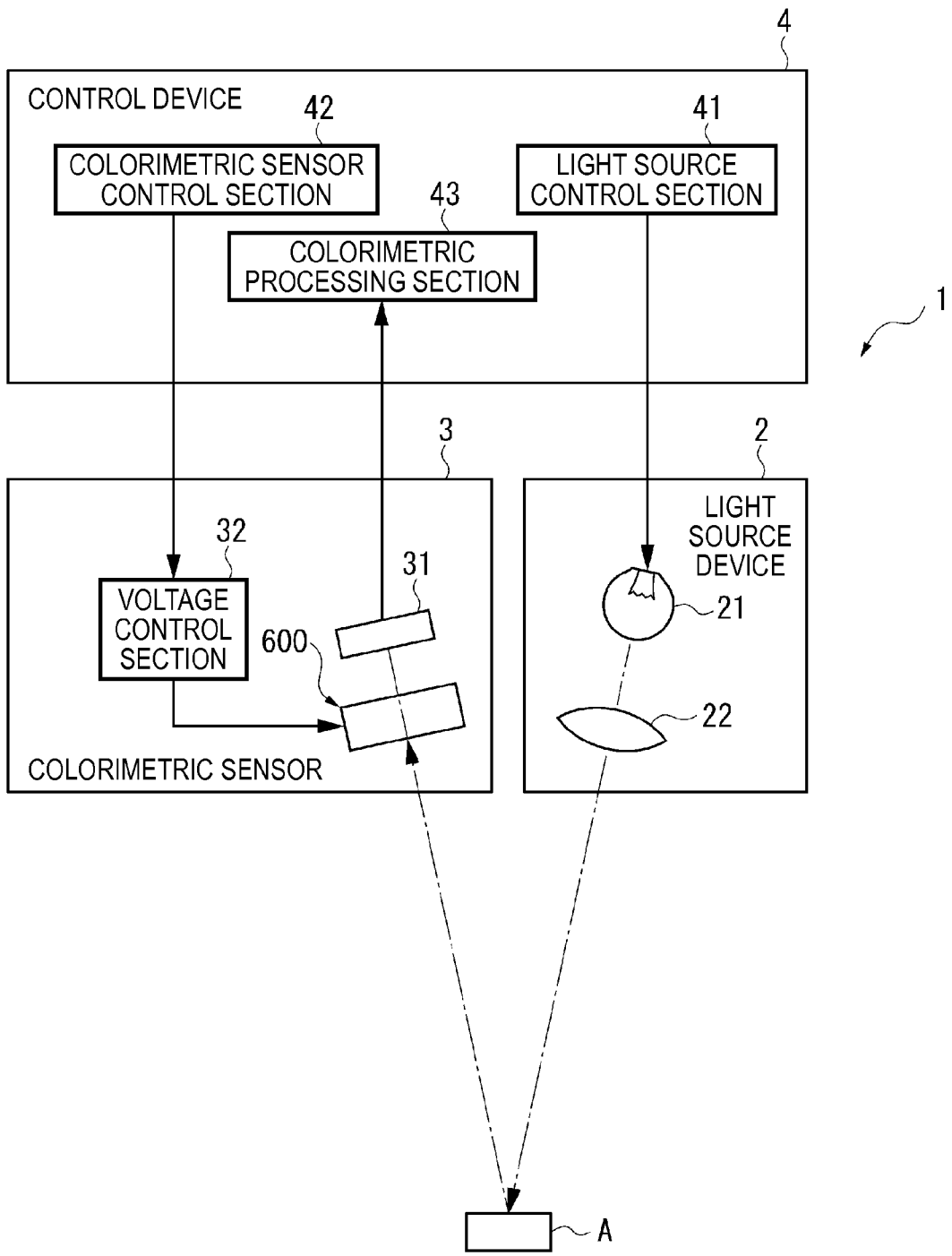
FIG. 1 is a block diagram showing a schematic configuration of a colorimetric device provided with an optical filter device according to a first embodiment of the invention.

FIG. 1 is a block diagram showing a schematic configuration of a colorimetric device 1 according to the first embodiment.

The colorimetric device 1 is encompassed in the electronic apparatus according to an aspect of the invention. As shown in FIG. 1, the colorimetric device 1 is provided with a light source device 2 for emitting light to a test object A, a colorimetric sensor 3, and a control device 4 for controlling an overall operation of the colorimetric device 1. Further, the colorimetric device 1 is a device for making the light, which is emitted from the light source device 2, be reflected by the test object A, receiving the test target light thus reflected using the colorimetric sensor 3, and analyzing and then measuring the chromaticity of the test target light, namely the color of the test object A, based on the detection signal output from the colorimetric sensor 3.

2. Configuration of Light Source Device

The light source device 2 is provided with a light source 21 and a plurality of lenses 22 (only one of the lenses is shown in FIG. 1), and emits a white light to the test object A. Further, it is possible for the plurality of lenses 22 to include a collimator lens, and in this case, the light source device 2 converts the white light emitted from the light source 21 into a parallel light with the collimator lens, and emits it from the projection lens not shown toward the test object A. It should be noted that although in the present embodiment the colorimetric device 1 provided with the light source device 2 is described as an example, in the case in which, for example, the test object A is a light emitting member such as a liquid crystal panel, it is also possible to adopt a configuration not provided with the light source device 2.

3. Configuration of Colorimetric Sensor

The colorimetric sensor 3 constitutes an optical module according to an aspect of the invention, and is provided with the optical filter device 600 having a variable wavelength interference filter 5 (see FIG. 4) according to an aspect of the invention. As shown in FIG. 1, the colorimetric sensor 3 is provided with the optical filter device 600, a detection section 31 for receiving the light transmitted through the variable wavelength interference filter 5 of the optical filter device 600, and a voltage control section 32 for varying the wavelength of the light to be transmitted through the variable wavelength interference filter 5. Further, the colorimetric sensor 3 is provided with an entrance optical lens (not shown) disposed at a position opposed to the variable wavelength interference filter 5, the entrance optical lens guiding the reflected light (the test target light), which has been reflected by the test object A, into the inside thereof. Further, the colorimetric sensor 3 disperses the light with a predetermined wavelength out of the test target light having entered from the entrance optical lens using the variable wavelength interference filter 5 in the optical filter device 600, and then receives the light thus dispersed using the detection section 31.

The detection section 31 is composed of a plurality of photoelectric conversion elements, and generates an electric signal corresponding to the received light intensity. Further, the detection section 31 is connected to the control device 4, and outputs the electric signal thus generated to the control device 4 as a light reception signal.

3-1. Configuration of Variable Wavelength Interference Filter

Figure 2:
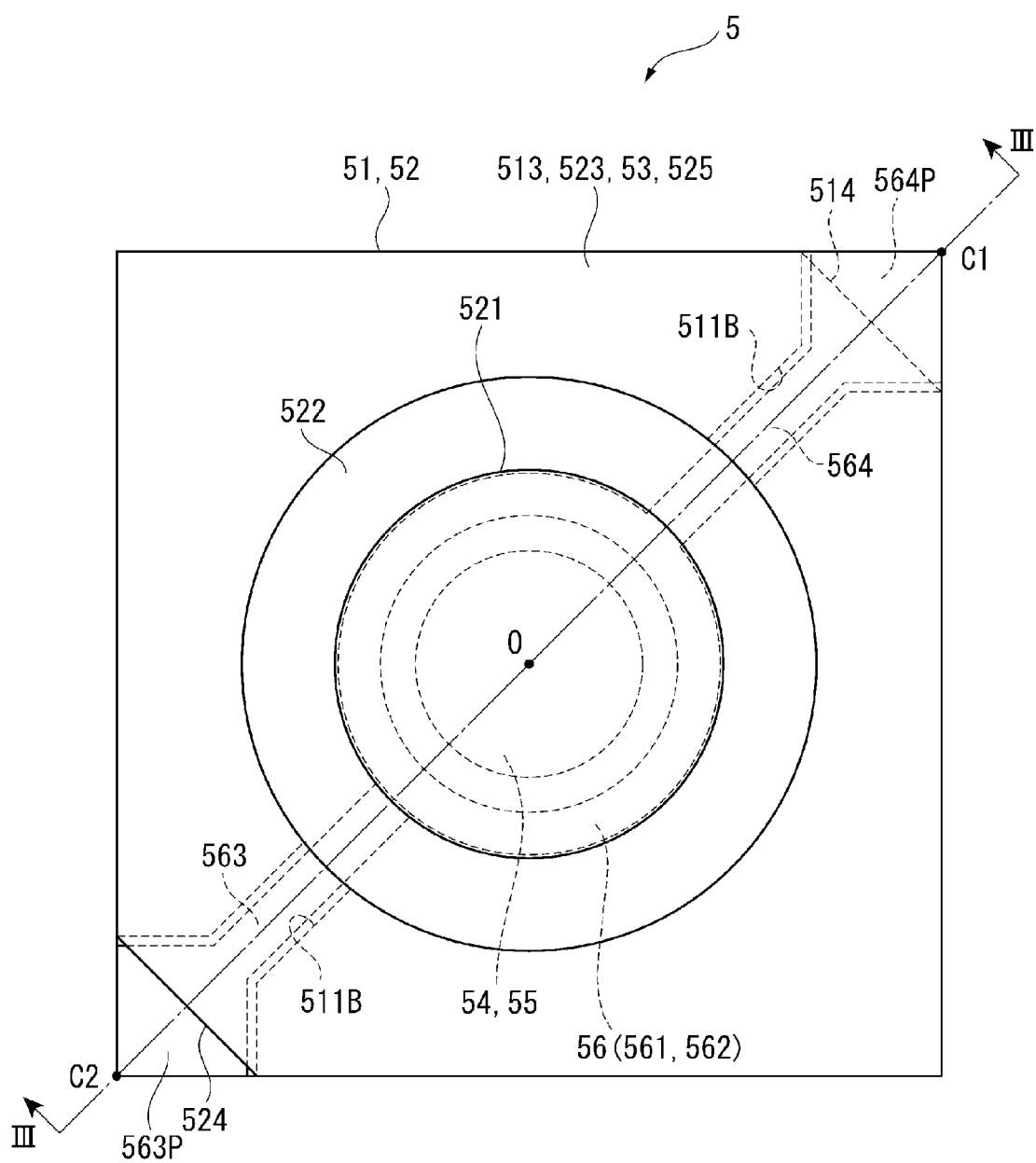
FIG. 2 is a plan view showing a schematic configuration of a variable wavelength interference filter according to the first embodiment.
Figure 3:
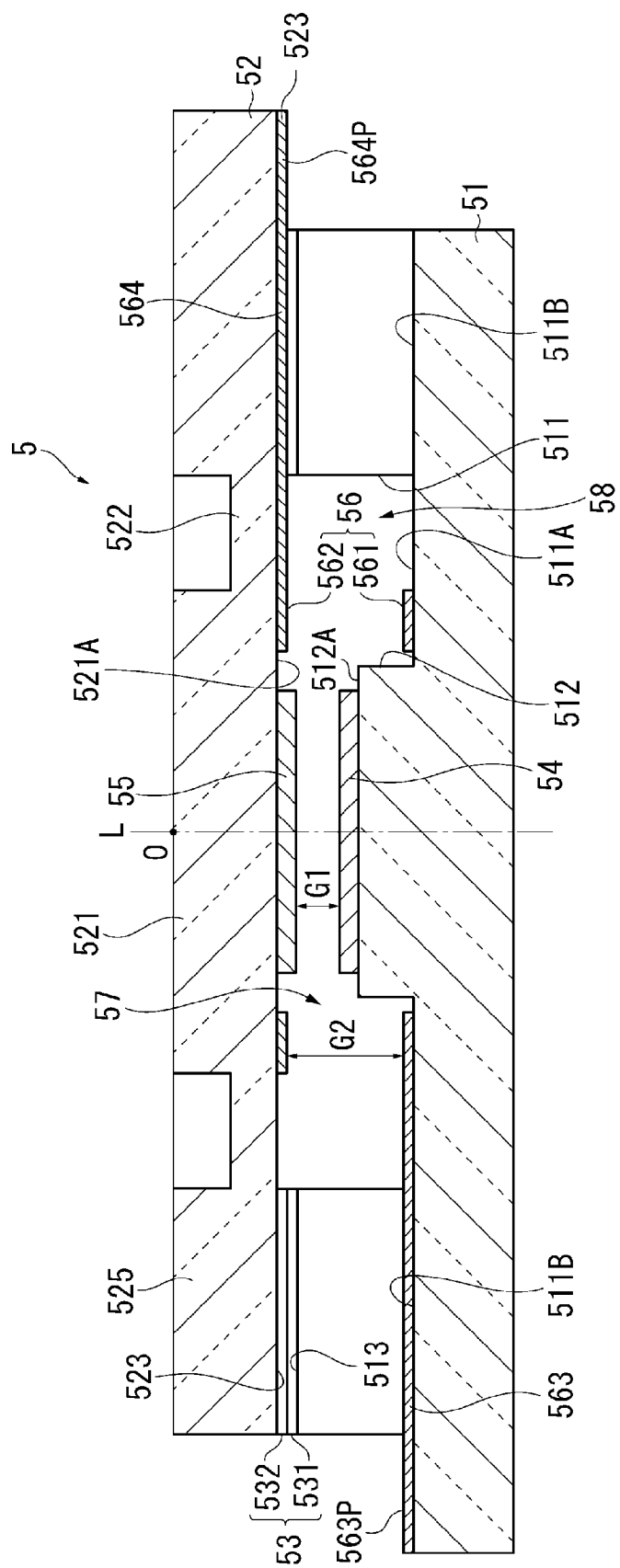
FIG. 3 is a cross-sectional view showing a schematic configuration of a variable wavelength interference filter according to the first embodiment.

FIG. 2 is a plan view showing a schematic configuration of the variable wavelength interference filter 5 provided to the optical filter device 600, and FIG. 3 is a cross-sectional view showing the schematic configuration of the variable wavelength interference filter 5.

As shown in FIG. 2, the variable wavelength interference filter 5 is, for example, an optical member having a rectangular shape. As shown in FIG. 3, the variable wavelength interference filter 5 is provided with a stationary substrate 51 as a first substrate according to an aspect of the invention, and a movable substrate 52 as a second substrate according to an aspect of the invention or a substrate. The stationary substrate 51 and the movable substrate 52 are each made of any of a variety of types of glass such as soda glass, crystalline glass, quartz glass, lead glass, potassium glass, borosilicate glass, or alkali-free glass, or a quartz crystal. Further, the stationary substrate 51 and the movable substrate 52 are configured integrally by bonding a first bonding section 513 of the stationary substrate 513 and a second bonding section 523 of the movable substrate 52 to each other with bonding films 53 (a first bonding film 531 and a second bonding film 532) each formed of, for example, a plasma polymerization film consisting primary of, for example, siloxane.

The stationary substrate 51 is provided with a stationary reflecting film 54 constituting the first reflecting film according to an aspect of the invention, and the movable substrate 52 is provided with a movable reflecting film 55 constituting the second reflecting film according to an aspect of the invention. The stationary reflecting film 54 and the movable reflecting film 55 are disposed so as to be opposed to each other across an inter-reflecting film gap G1. Further, the variable wavelength interference filter 5 is provided with an electrostatic actuator 56 used for adjusting (varying) the gap amount (the distance between the reflecting films, the dimension between the reflecting films) of the inter-reflecting film gap G1. The electrostatic actuator 56 corresponds to a gap amount varying section (a distance varying section) according to an aspect of the invention. The electrostatic actuator 56 is constituted by a stationary electrode 561 provided to the stationary substrate 51 and a movable electrode 562 provided to the movable substrate 52. The stationary electrode 561 and the movable electrode 562 are opposed to each other across an inter-electrode gap G2. Here, there can be adopted a configuration of disposing these electrodes 561, 562 directly on the surfaces of the stationary substrate 51 and the movable substrate 52, respectively, or a configuration of disposing them by way of other film members. Here, the gap amount of the inter-electrode gap G2 is larger than the gap amount of the inter-reflecting film gap G1.

Further, in a filter plan view shown in FIG. 2 in which the variable wavelength interference filter 5 is viewed from the thickness direction of the stationary substrate 51 (the movable substrate 52), the planar center point O of the stationary substrate 51 and the movable substrate 52 coincides with the center point of the stationary reflecting film 54 and the movable reflecting film 55, and further coincides with the center point of a movable section 521 described later.

It should be noted that in the explanation below, the plan view from the thickness direction of the stationary substrate 51 or the movable substrate 52, namely the plan view of the variable wavelength interference filter 5 viewed from the stacking direction of the stationary substrate 51, the bonding film 53, and the movable substrate 52, is referred to as the filter plan view.

3-1-1. Configuration of Stationary Substrate

The stationary substrate 51 is formed by processing a glass substrate formed to have a thickness of, for example, 500 μm. Specifically, as shown in FIG. 3, the stationary substrate 51 is provided with an electrode arrangement groove 511 and a reflecting film installation section 512 by etching. The stationary substrate 51 is formed to have a thickness dimension larger than that of the movable substrate 52, and there is no deflection of the stationary substrate 51 due to the electrostatic attractive force when applying a voltage between the stationary electrode 561 and the movable electrode 562, or the internal stress of the stationary electrode 561.

Further, a vertex C1 of the stationary substrate 51 is provided with a cutout section 514, and a movable electrode pad 564P described later is exposed on the stationary substrate 51 side of the variable wavelength interference filter 5.

The electrode arrangement groove 511 is formed to have a ring-like shape cantered on the planar center point O of the stationary substrate 51 in the filter plan view. The reflecting film installation section 512 is formed so as to protrude toward the movable substrate 52 side from the central portion of the electrode arrangement groove 511 in the plan view described above. Here, the bottom surface of the electrode arrangement groove 511 forms an electrode installation surface 511A on which the stationary electrode 561 is disposed. Further, the projection tip surface of the reflecting film installation section 512 forms a reflecting film installation surface 512A.

Further, the stationary substrate 51 is provided with electrode extraction grooves 511B respectively extending from the electrode arrangement groove 511 toward the vertexes C1, C2 of the outer peripheral edge of the stationary substrate 51.

The electrode installation surface 511A of the electrode arrangement groove 511 is provided with the stationary electrode 561. More specifically, the stationary electrode 561 is disposed in an area of the electrode installation surface 511A, the area being opposed to the movable electrode 562 of the movable section 521 described later. Further, it is also possible to adopt the configuration in which an insulating film for providing an insulation property between the stationary electrode 561 and the movable electrode 562 is stacked on the stationary electrode 561.

Further, the stationary substrate 51 is provided with a stationary extraction electrode 563 extending from the outer peripheral edge of the stationary electrode 561 toward the vertex C2. The extending tip portion (a part located at the vertex C2 of the stationary substrate 51) of the stationary extraction electrode 563 forms a stationary electrode pad 563P connected to the voltage control section 32.

It should be noted that although in the present embodiment there is shown a configuration of providing the single stationary electrode 561 to the electrode installation surface 511A, it is also possible to adopt, for example, a configuration (a dual electrode structure) in which two concentric electrodes cantered on the planar center point O are provided.

As described above, the reflecting film installation section 512 is formed to have a roughly columnar shape coaxial with the electrode arrangement groove 511 and having a diameter smaller than that of the electrode arrangement groove 511, and is provided with the reflecting film installation surface 512A opposed to the movable substrate 52 of the reflection film installation section 512.

As shown in FIG. 3, the stationary reflecting film 54 is installed in the reflecting film installation section 512. As the stationary reflecting film 54, a metal film made of, for example, Ag, or an alloy film made of, for example, an Ag alloy can be used. Further, it is also possible to use a dielectric multilayer film with a high refractive index layer made of, for example, $TiO_2$, and a low refractive index layer made of, for example, $SiO_2$. Further, it is also possible to use a reflecting film obtained by stacking a metal film (or an alloy film) on a dielectric multilayer film, a reflecting film obtained by stacking a dielectric multilayer film on a metal film (or an alloy film), a reflecting film obtained by laminating a single refractive layer (made of, e.g., $TiO_2$ or $SiO_2$) and a metal film (or an alloy film) with each other, and so on.

Further, it is also possible to form an antireflection film on the light entrance surface (the surface not provided with the stationary reflecting film 54) of the stationary substrate 51 at a position corresponding to the stationary reflecting film 54. The antireflection film can be formed by alternately stacking low refractive index films and high refractive index films, decreases the reflectance of the visible light on the surface of the stationary substrate 51, and increases the transmittance thereof.

Further, the surface not provided with the electrode arrangement groove 511, the reflecting film installation section 512, and the electrode extraction grooves 511B by etching out of the surfaces of the stationary substrate 51 opposed to the movable substrate 52 constitutes a first bonding section 513. The first bonding section 513 is provided with a first bonding film 531, and by bonding the first bonding film 531 to a second bonding film 532 provided to the movable substrate 52, the stationary substrate 51 and the movable substrate 52 are bonded to each other.

3-1-2. Configuration of Movable Substrate

The movable substrate 52 is formed by processing a glass substrate formed to have a thickness of, for example, 200 μm.

Specifically, the movable substrate 52 is provided with a movable section 521 having a circular shape centered on the planar center point O in the filter plan view shown in FIG. 2, a holding section 522 coaxial with the movable section 521 and for holding the movable section 521, and a substrate peripheral section 525 disposed on the outer side of the holding section 522.

Further, as shown in FIG. 2, in the movable substrate 52, there is formed a cutout section 524 in accordance with the vertex C2, and when viewing the variable wavelength interference filter 5 from the movable substrate 52 side, the stationary electrode pad 563P is exposed.

The movable section 521 is formed to have a thickness dimension larger than that of the holding section 522, and is formed in the present embodiment, for example, to have the same thickness dimension as that of the movable substrate 52. The movable section 521 is formed to have a diameter larger than at least the diameter of the outer peripheral edge of the reflecting film installation surface 512A in the filter plan view. Further, the movable section 521 is provided with the movable electrode 562 and the movable reflecting film 55.

It should be noted that it is also possible to form an antireflection film on the opposite surface of the movable section 521 to the stationary substrate 51 similarly to the case of the stationary substrate 51. Such an antireflection film can be formed by alternately stacking low refractive index films and high refractive index films, can decrease the reflectance of the visible light on the surface of the stationary substrate 52, and can increase the transmittance thereof.

The movable electrode 562 is opposed to the stationary electrode 561 across the inter-electrode gap G2, and is formed to have an annular shape, which is the same shape as that of the stationary electrode 561. Further, the movable substrate 52 is provided with a movable extraction electrode 564 extending from the outer peripheral edge of the movable electrode 562 toward the vertex C1 of the movable substrate 52. The extending tip portion (a part located at the vertex C1 of the movable substrate 52) of the movable extraction electrode 564 forms a movable electrode pad 564P connected to the voltage control section 32.

The movable reflecting film 55 is disposed at the central portion of a movable surface 521A of the movable section 521 so as to be opposed to the stationary reflecting film 54 across the inter-reflecting film gap G1. As the movable reflecting film 55, a reflecting film having the same configuration as that of the stationary reflecting film 54 described above is used.

Here, the gap amount of the inter-electrode gap G2 is larger than the gap amount of the inter-reflecting film gap G1.

The holding section 522 is a diaphragm surrounding the periphery of the movable section 521, and is formed to have a thickness dimension smaller than that of the movable section 521.

Such a holding section 522 is easier to be deflected than the movable section 521, and it becomes possible to displace the movable section 521 toward the stationary substrate 51 with a weak electrostatic attractive force. On this occasion, since the movable section 521 has a larger thickness dimension and higher rigidity than those of the holding section 522, the shape variation of the movable section 521 does not occur even in the case in which the holding section 522 is pulled toward the stationary substrate 51 due to the electrostatic attractive force. Therefore, deflection of the movable reflecting film 55 provided to the movable section 521 does not occur, and it becomes possible to always keep the stationary reflecting film 54 and the movable reflecting film 55 in a parallel state.

It should be noted that although in the present embodiment the holding section 522 having a diaphragm shape is shown as an example, the shape is not limited thereto, but a configuration of, for example, providing beam-like holding sections arranged at regular angular intervals centered on the planar center point O can also be adopted.

As described above, the substrate peripheral section 525 is disposed on the outer side of the holding section 522 in the filter plan view. The surface of the substrate peripheral section 525 opposed to the stationary substrate 51 is provided with the second bonding section 523 opposed to the first bonding section 513. Further, the second bonding section 523 is provided with the second bonding film 532, and as described above, by bonding the second bonding film 532 to the first bonding film 531, the stationary substrate 51 and the movable substrate 52 are bonded to each other.

In such a variable wavelength interference filter 5 as described above, the dimension of the gap between the electrode installation surface 511A of the electrode arrangement groove 511 and the surface of the movable substrate 52 opposed to the stationary substrate 51 is formed to be larger than the dimension (the gap amount) of the inter-reflecting film gap G1, and the space formed between the electrode installation surface 511A and the movable substrate 52 constitutes a releasing space 57. Specifically, when applying a voltage to the electrostatic actuator 56 to thereby displace the movable section 521 toward the stationary substrate 51, the air (the air existing in the inter-reflecting film gap G1) sandwiched between the reflecting film installation surface 512A and the movable surface 521A is pushed outside, and escapes to the releasing space 57. It should be noted that the releasing space 57 is a space contiguous to the inter-reflecting film gap G1, and specifically, corresponds to a space (including the inter-electrode gap G2) between the movable section 521 and the electrode arrangement groove 511 and a space between the holding section 522 and the electrode arrangement groove 511.

Further, in the present embodiment, a filter internal space 58 including the inter-reflecting film gap G1 and the releasing space 57 communicates with the outside of the variable wavelength interference filter 5 by way of the electrode extraction grooves 511B. In other words, in the present embodiment, the electrode extraction grooves 511B constitute a communication section according to an aspect of the invention.

3-2. Configuration of Optical Filter Device

Then, the configuration of the optical filter device 600 will be explained with reference to the accompanying drawings.

Figure 4:
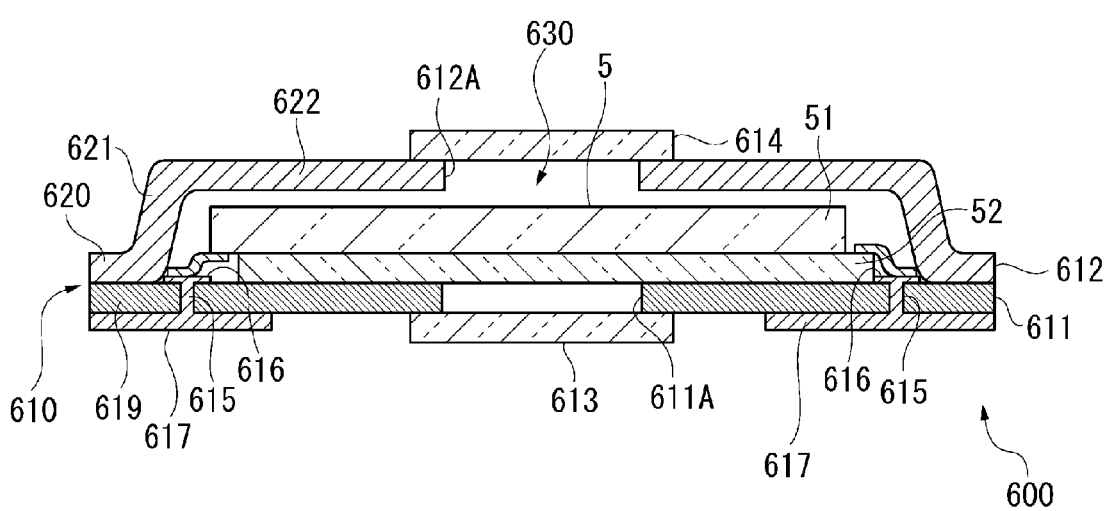
FIG. 4 is a cross-sectional view showing a schematic configuration of an optical filter device according to the first embodiment.

FIG. 4 is a cross-sectional view showing the schematic configuration of the optical filter device 600.

As shown in FIG. 4, the optical filter device 600 is provided with a housing 610 for housing the variable wavelength interference filter 5.

The housing 610 has a bottom section 611, a lid 612, an entrance side glass window 613 (a light guide section), and an exit side glass window 614 (a light guide section).

The bottom section 611 is formed of, for example, a single layer ceramic substrate. The bottom section 611 is provided with the movable substrate 52 of the variable wavelength interference filter 5. Further, the bottom section 611 is provided with a light entrance hole 611A formed in an area opposed to the reflecting films (the stationary reflecting film 54, the movable reflecting film 55) of the variable wavelength interference filter 5. The light entrance hole 611A is a window through which the incident light (the test target light) to be dispersed by the variable wavelength interference filter 5 enters, and is provided with the entrance side glass window 613 bonded thereto. It should be noted that as the method of bonding the bottom section 611 and the entrance side glass window 613 to each other, there can be used the glass frit bonding method using a glass frit, which is a scrap of glass obtained by melting glass material at high temperature and then rapidly cooling it. In such glass frit bonding, no gap occurs between the bottom section 611 and the entrance side glass window 613, and the inside of the housing 610 can be made airtight.

Further, the corresponding number of terminal sections 616 to the electrode pads 563P, 564P of the variable wavelength interference filter 5 is disposed on the upper surface (on the inner side of the housing 610) of the bottom section 611. Further, the bottom section 611 is provided with through holes 615 formed at positions where the respective terminal sections 616 are disposed, and the terminal sections 616 are connected to connection terminals 617 disposed on the lower surface (on the outer side of the housing 610) of the bottom section 611 by way of the through holes 615, respectively. Here, the through holes 615 are filled with the metal material (e.g., Ni and Au) for connecting the terminal sections 616 and the connection terminals 617 to thereby be sealed.

Further, each of the connection terminals 617 is connected to the voltage control section 32, and thus, it becomes possible to apply the voltage to the electrostatic actuator 56 of the variable wavelength interference filter 5.

Further, the outer peripheral edge of the bottom section 611 is provided with a sealing section 619 bonded to the lid 612.

As shown in FIG. 4, the lid 612 is provided with a sealing section 620 bonded to the sealing section 619 of the bottom section 611, a sidewall section 621 continuous from the sealing section 620 and rising in the direction of getting away from the bottom section 611, and a top surface section 622 continuous from the sidewall section 621 and covering the stationary substrate 51 side of the variable wavelength interference filter 5. The lid 612 can be formed of an alloy such as kovar, or metal.

The lid 612 is tightly bonded to the bottom section 611 by bonding the sealing section 620 and the sealing section 619 of the bottom section 611 to each other using, for example, laser sealing. Further, the top surface section 622 of the lid 612 is provided with a light exit hole 612A formed in an area opposed to the reflecting films 54, 55 of the variable wavelength interference filter 5. The light exit hole 612A is a window through which the light dispersed by the variable wavelength interference filter 5 and then taken out passes, and an exit side glass window 614 is tightly bonded thereto using, for example, glass frit bonding.

In such an optical filter device 600 as described above, the housing 610 is configured so that the internal space 630 in which the variable wavelength interference filter 5 is housed becomes airtight, and is kept in the reduced pressure state (with the pressure $P_0$).

Further, the filter internal space 58 of the variable wavelength interference filter 5 including the inter-reflecting film gap G1 and the releasing space 57 communicates with an internal space 630 of the housing 610 by way of the electrode extraction grooves 511B as the communication section. Therefore, the pressure of the filter internal space 58 is also kept to the same pressure ($P_0$) as in the internal space 630 of the housing 610.

Here, assuming that the spring constant of the holding section 522 is $k_v$, and the spring constant of the air spring due to the air existing in the inter-reflecting film gap G1 is $k_{air}$, the pressure $P_0$ is set to a value satisfying the following relationship (the relationship of Formula (1) described above).

$$k_v \geq 20 \times k_{air}$$

3-3. Setting of Internal Pressure of Housing

Then, the internal pressure (the pressure of the filter internal space 58) of the housing 610 will be explained.

The gap amount of the inter-reflecting film gap G1 of the variable wavelength interference filter 5 according to the present embodiment described above is adjusted by displacing the movable section 521 using the electrostatic attractive force caused by applying the step voltage to the electrostatic actuator 56.

Figure 5:
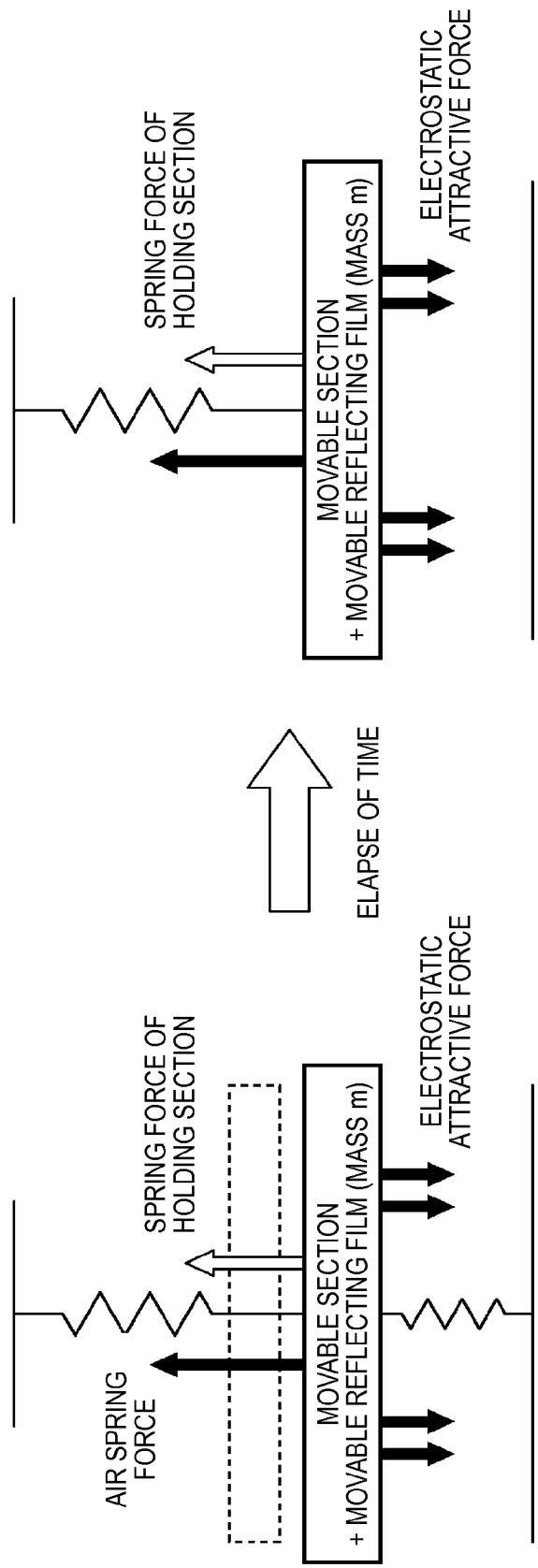
FIG. 5 is an explanatory diagram for explaining the state of the force acting on a movable section when displacing the movable section.

FIG. 5 is an explanatory diagram for explaining the state of the force acting on the movable section 521 when displacing the movable section 521 by the electrostatic attractive force.

As shown in the left diagram of FIG. 5, when displacing the movable section 521, the spring force of the holding section 522 generated by deflecting the holding section 522, and the spring force (the air spring force) of the air spring generated by compressing the air (the air existing in the inter-reflecting film gap G1) between the movable section 521 and the reflecting film installation section 512 act on the movable section 521. Due to these spring forces, the movable section 521 repeats vibration immediately after the application of the voltage for a predetermined period of time.

Here, assuming that the total mass of the movable section 521 and the movable reflecting film 55 is m, the spring constant of the holding section 522 is $k_v$, and the spring constant of the air spring is $k_{air}$, the characteristic period of the vibration of the movable section 521 is expressed by Formula (2) below.

$$T = 2\pi \sqrt{\frac{m}{k_v + k_{air}}} \qquad (2)$$

Further, the spring constant of the air spring $k_{air}$ is obtained by the Boyle's law, and is a value proportional to the pressure, and is expressed by Formula (3) below.

$$k_{air} = \frac{S_v}{h_v - x} \times P_0 \qquad (3)$$

In Formula (3), $S_v$ denotes the plane area on which the air spring acts, and corresponds to the area of the reflecting film installation surface 512A. Further, $h_v$ denotes an initial gap amount of the inter-reflecting film gap G1, x denotes a variation in the gap amount of the inter-reflecting film gap G1, and $P_0$ denotes the pressure of the air existing in the inter-reflecting film gap G1 in the initial state.

As described above, when varying the gap amount of the inter-reflecting film gap G1, the movable section 521 vibrates at the characteristic period T represented by Formula (2), and the vibration attenuates over time. On the other hand, when the gap amount of the inter-reflecting film gap G1 is reduced, the air spring force with the spring constant $k_{air}$ acts thereon due to the compression of the air existing in the inter-reflecting film gap G1, and the air spring force attenuates as the air existing in the inter-reflecting film gap G1 escapes to the releasing space 57. In particular, in such a variable wavelength interference filter as in the present embodiment, the initial gap amount of the inter-reflecting film gap G1 is set to, for example, 400 nm, while the reflecting films 54, 55 are formed to have the diameter of, for example, about 3 mm. In such a configuration, when reducing the gap amount of the inter-reflecting film gap G1, the air existing in the inter-reflecting film gap G1 fails to immediately escape to the releasing space 57. Therefore, in such a variable wavelength interference filter 5, it results that the air spring force of the air existing in the inter-reflecting film gap G1 acting on the movable section 521 attenuates gradually. Further, it eventually results that the air spring force does not affect the movable section 521 as shown in the right diagram of FIG. 5.

In other words, the gap amount stabilization time until the light with the target wavelength can stably be taken out by the variable wavelength interference filter 5 is related to the time until the action of the air spring force on the movable section 521 vanishes in addition to the time until the vibration of the movable section 521 stops. Further, the time until the action of the air spring force on the movable section 521 varies in accordance with the internal pressure (the pressure of the filter internal space 58) of the housing 610.

Figure 6:
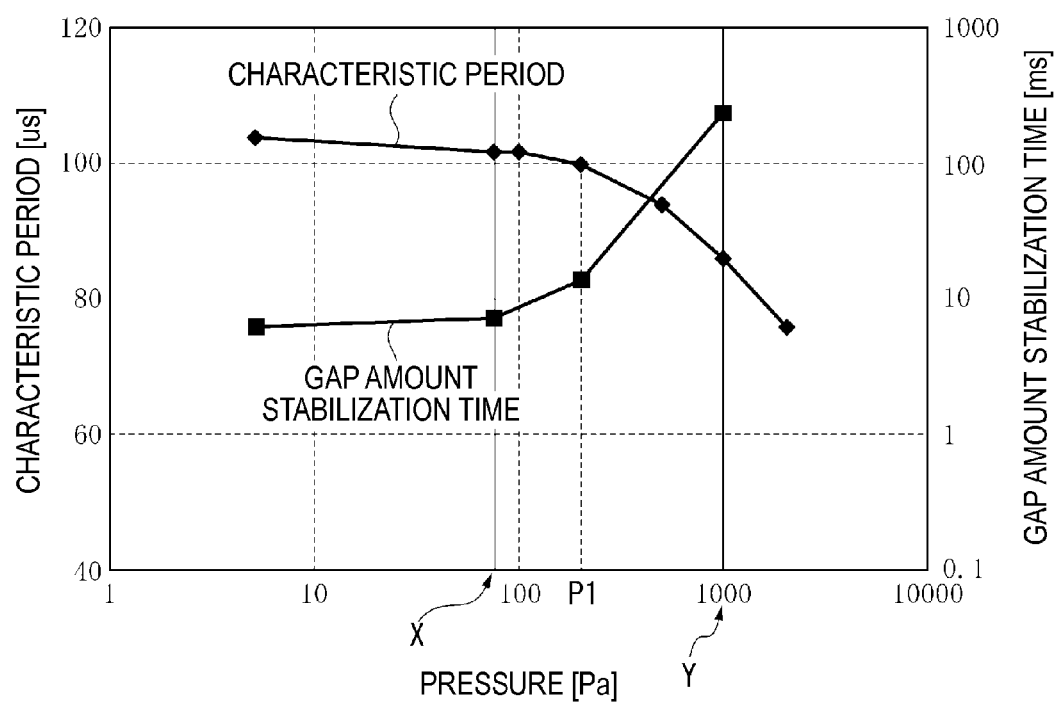
FIG. 6 is a diagram showing a relationship between the pressure of a filter internal space and a characteristic period of the movable section, and a relationship between the pressure of the filter internal space and gap amount stabilization time.

FIG. 6 is a diagram showing a relationship between the internal pressure (the pressure of the filter internal space 58) of the housing 610 and the characteristic period of the movable section 521, and a relationship between the internal pressure (the pressure of the filter internal space) of the housing 610 and the gap amount stabilization time. Further, FIGS. 7A through 7C are diagrams showing a relationship between the time and the gap amount of the inter-reflecting film gap G1 in the case of the state X (the characteristic period T is 104 μm) shown in FIG. 6, and FIGS. 8A through 8C are diagrams showing a relationship between the time and the gap amount of the inter-reflecting film gap G1 in the case of the state Y (the characteristic period T is 86 μm) shown in FIG. 6.

Figure 7A:
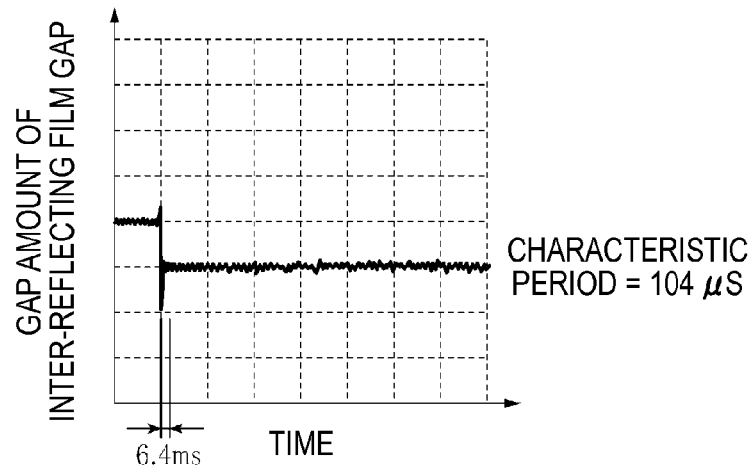
FIGS. 7A through 7C are diagrams showing a relationship between the time and the gap amount of an inter-reflecting film gap in the state X in FIG. 6.
Figure 7B:
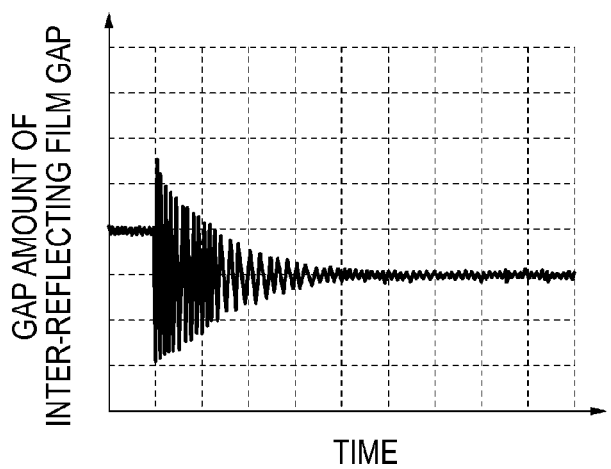
Figure 7C:
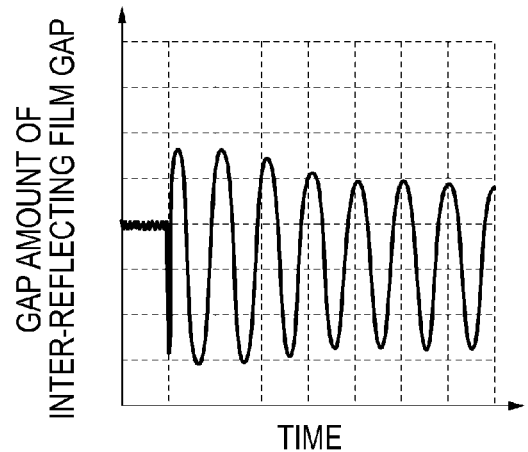
Figure 8A:
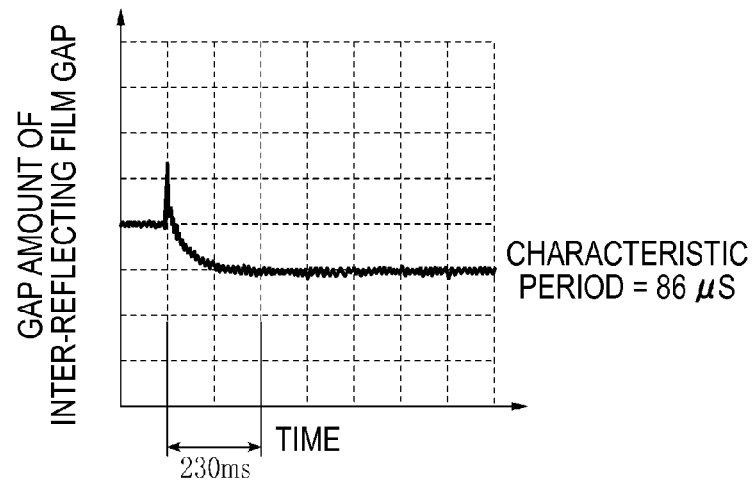
FIGS. 8A through 8C are diagrams showing a relationship between the time and the gap amount of the inter-reflecting film gap in the state Y in FIG. 6.
Figure 8B:
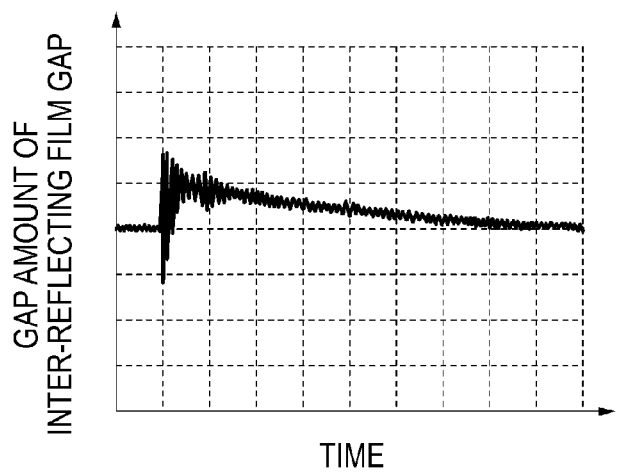
Figure 8C:
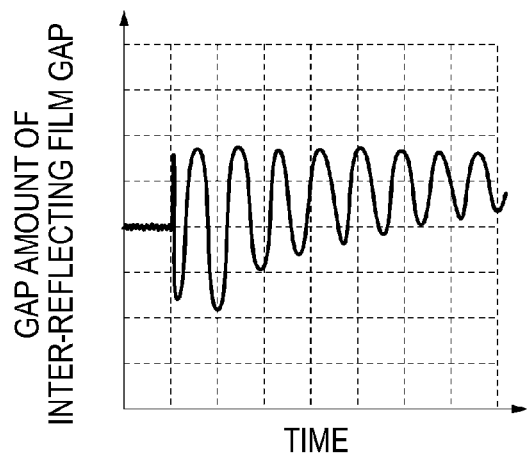

It should be noted that in FIGS. 7A through 7C, and 8A through 8C, FIGS. 7B and 8B are enlarged views of the parts (immediately after starting the vibration) shown in FIGS. 7A and 8A, respectively, and FIGS. 7C and 8C are further enlarged views of the parts (immediately after starting the vibration) shown in FIGS. 7B and 8B, respectively.

As shown in FIG. 6, when varying the internal pressure of the housing 610, the vibration form of the movable section 521 can be divided into two patterns at the boundary of a predetermined pressure P1.

Specifically, in the case in which the pressure is equal to or lower than P1, the characteristic period T and the gap amount stabilization time hardly vary. In the explanation below, this vibration form is referred to as a mode A. In mode A, as shown in, for example, FIGS. 7A through 7C, when the movable section 521 vibrates at the characteristic period T, and then the vibration attenuates overtime and then converges, the gap amount variation in the inter-reflecting film gap G1 vanishes. Here, in an example (FIGS. 7A through 7C) of mode A, if the characteristic period T is 104 μm, the gap amount stabilization time is 6.4 ms.

In contrast, in the case in which the pressure exceeds P1, as the pressure is increased, the characteristic period T rapidly decreases, and the gap amount stabilization time increases rapidly. In the explanation below, this vibration form is referred to as a mode B. In mode B, as shown in FIGS. 8A through 8C, after the movable section 521 vibrates at the characteristic period T, the vibration attenuates over time similarly to mode A. However, even after the vibration has converged, the gap amount variation in the inter-reflecting film gap G1 occurs. Here, in an example (FIGS. 8A to 8C) of mode B, if the characteristic period T is 86 μm, the gap amount stabilization time is 230 ms, and the gap amount stabilization time is extremely longer in mode B compared to mode A.

In such a mode B, the air existing in the inter-reflecting gap G1 is in the compressed state at the time when the vibration of the movable section 521 has converged, and the air affects the movable section 521 as the air spring. Therefore, the gap amount variation in the inter-reflecting film gap G1 occurs. In other words, even after the vibration has converged, the gap amount variation of the inter-reflecting film gap G1 occurs until the air existing in the inter-reflecting film gap G1 escapes to the releasing space 57 and the air spring force acting on the movable section 521 vanishes.

If such a mode B as described above occurs, even if the response is improved by reducing the internal pressure of the housing 610 in the variable wavelength interference filter 5, the gap amount stabilization time is increased, and as a result, prompt execution of measurement is not achievable. Further, although it is possible to prevent or suppress the occurrence of mode B by making the internal space 630 (the filter internal space 58) of the housing 610 a vacuum, it incurs increase in manufacturing cost to create the vacuum condition in the inside of the housing 610. Further, in order to keep the vacuum, it is required to increase the bonding strength of the bottom section 611 and the lid 612, the bonding strength of the bottom section 611 and the entrance side glass window 613, and the bonding strength of the lid 612 and the exit side glass window 614, and from this point of view, it is possible to incur increase in manufacturing cost, or degradation of production efficiency.

Therefore, the inventors of the invention have newly found out that mode B is excluded in the case in which the requirement of Formula (1) described above is satisfied without making the internal space 630 (the filter internal space 58) of the housing 610 a vacuum based on experiments. The content thereof will hereinafter be described in detail based on FIGS. 9 and 10.

Figure 9:
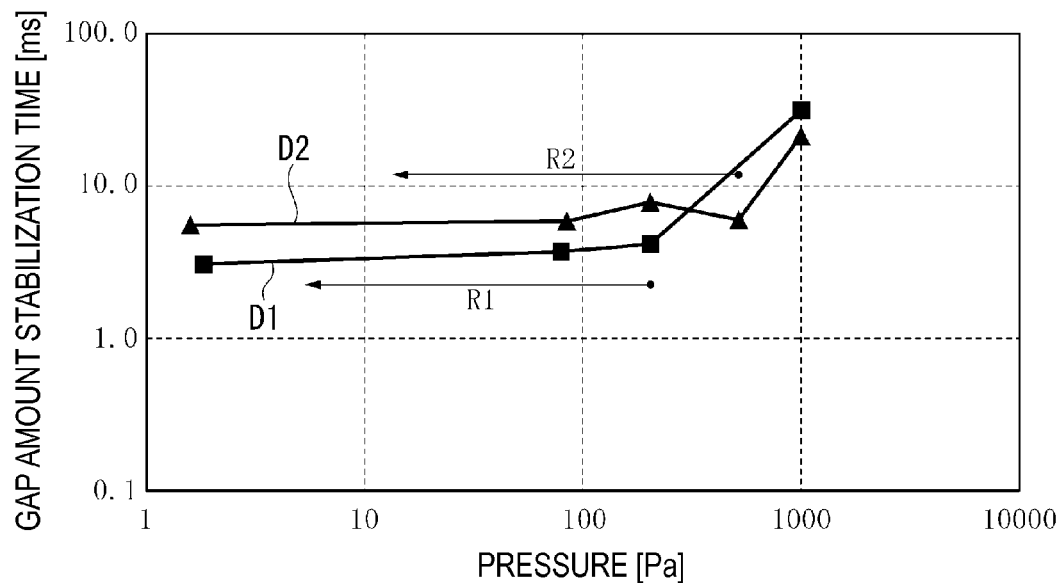
FIG. 9 is a diagram showing a relationship between the pressure of the filter internal space and the gap amount stabilization time.
Figure 10:
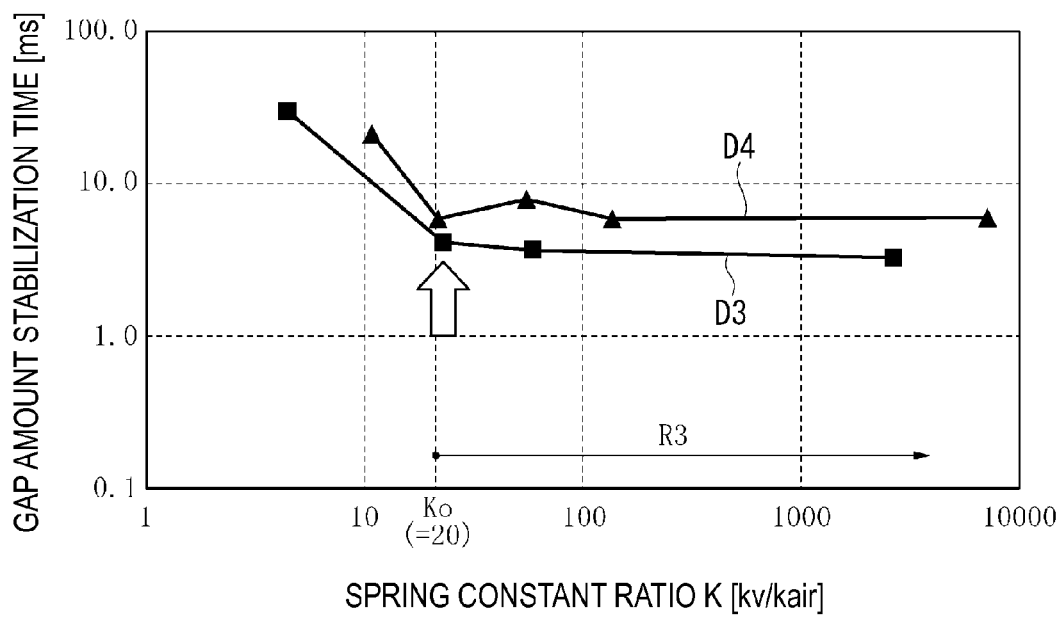
FIG. 10 is a diagram showing a relationship between the spring constant ratio and the gap amount stabilization time.

FIGS. 9 and 10 are diagrams showing a variation of the gap amount stabilization time in the case of varying the conditions of the spring constant $k_v$ of the holding section 522 and the spring constant $k_{air}$ of the air spring, wherein FIG. 9 is a diagram showing a relationship between the internal pressure (the pressure of the filter internal space 58) of the housing 610 and the gap amount stabilization time. FIG. 10 is a diagram obtained by converting the horizontal axis of FIG. 9 into a spring constant ratio K (the ratio between the spring constant $k_v$ of the holding section 522 and the spring constant $k_{air}$ of the air spring).

It should be noted that in FIG. 9, the measurement result of the gap amount stabilization time when varying the internal pressure (the pressure of the filter internal space 58) of the housing 610 with respect to the variable wavelength interference filter 5 with the spring constant of the holding section 522 of $k_v$ is indicated by data D1, and the range of the pressure in which the movable section 521 is in the vibration form of mode A is indicated by the arrow R1. Further, the measurement result of the gap amount stabilization time when varying the internal pressure (the pressure of the filter internal space 58) of the housing 610 with respect to the variable wavelength interference filter 5 with the spring constant of the holding section 522 of $2.5 \times k_v$ is indicated by data D2, and the range of the pressure in which the movable section 521 is in the vibration form of mode A is indicated by the arrow R2. Further, in FIG. 10, the data D3 is the data obtained by converting the data D1, the data D4 is the data obtained by converting the data D2, and the range of the spring constant ratio K in which the movable section 521 is in the vibration form of mode A is indicated by R3.

As indicated by R1, R2, the range of the pressure in which mode B is prevented from occurring varies with the spring constant of the holding section 522. On the other hand, if FIG. 9 is converted into the spring constant ratio as shown in FIG. 10, the vibration form of mode A appears in the case (the range of R3 in FIG. 10) in which the spring constant ratio K is equal to or larger than a critical point $K_0$ taking the predetermined critical point $K_0$ (=20) as a boundary of the spring constant ratio K in either of the cases. It should be noted that although FIGS. 9 and 10 show only two typical experimental results, even in the case of setting the spring constant $k_v$ of the holding section 522 and the spring constant $k_{air}$ of the air spring to other conditions, substantially the same data can be obtained.

Further, based on the knowledge described above, the internal pressure $P_0$ of the housing 610 of the present embodiment is set to the value satisfying Formula (1) described above in order to prevent or suppress the occurrence of the vibration form of mode B. Further, by calculating a specific numerical value of the pressure $P_0$ based on Formula (3), Formula (4) below is obtained.

$$P_0 \leq \frac{k_v \times (h_v - x)}{20 \times S_v} \quad (4)$$

Here, x denotes a value set in accordance with the wavelength band of the light which can be taken out by the variable wavelength interference filter 5, and it is possible to substitute, for example, the maximum variation of the movable section 521 for x. Further, the smaller the amount of pressure reduction of the internal pressure of the housing 610 is, the lower the manufacturing cost is, and the more the production efficiency is improved. Therefore, in the present embodiment, the following is set as the internal pressure $P_0$ of the housing 610.

$$P_0 = k_v \times (h_v - x)/20 S_v$$

3-4. Configuration of Voltage Control Section

The voltage control section 32 is connected to the stationary electrode pad 563P and the movable electrode pad 564P by way of the connection terminals 617 and the terminal sections 616. Further, the voltage control section 32 applies a predetermined step voltage between the stationary electrode pad 563P and the movable electrode pad 564P based on a control signal input from the control device 4 to thereby drive the electrostatic actuator 56. Thus, the electrostatic attractive force is generated in the inter-electrode gap G2, the holding section 522 is deflected to thereby displace the movable section 521 toward the stationary substrate 51, and thus it becomes possible to set the inter-reflecting film gap G1 to the desired gap amount.

4. Configuration of Control Device

The control device 4 controls an overall operation of the colorimetric device 1.

As the control device 4, a general-purpose personal computer, a handheld terminal, a colorimetry-dedicated computer, and so on can be used.

Further, as shown in FIG. 1, the control device 4 is configured including a light source control section 41, a colorimetric sensor control section 42, a colorimetric processing section 43, and so on.

The light source control section 41 is connected to the light source device 2. Further, the light source control section 41 outputs a predetermined control signal to the light source device 2 based on, for example, a setting input by the user to thereby make the light source device 2 emit a white light with a predetermined brightness.

The colorimetric sensor control section 42 is connected to the colorimetric sensor 3. Further, the colorimetric sensor control section 42 sets the wavelength of the light to be received by the colorimetric sensor 3 based on, for example, the setting input by the user, and then outputs the control signal, which instructs the detection of the intensity of the received light having the wavelength thus set, to the colorimetric sensor 3. Thus, the voltage control section 32 of the colorimetric sensor 3 sets the voltage to be applied to the electrostatic actuator 56 based on the control signal so as to transmit only the light having the wavelength desired by the user.

The colorimetric processing section 43 analyzes the chromaticity of the test object A based on the light reception intensity detected by the detection section 31.

5. Functions and Advantages of First Embodiment

The variable wavelength interference filter 5 according to the present embodiment is provided with the releasing space 57 as the space to which the air existing in the inter-reflecting film gap G1 escapes when varying the gap amount of the inter-reflecting film gap G1 between the stationary reflecting film 54 and the movable reflecting film 55 using the electrostatic actuator 56. Further, the pressure $P_0$ of the filter internal space 58 of the variable wavelength interference filter 5 is set so as to fulfill the condition ($k_v \geq 20 k_{air}$) of Formula (1) described above assuming that the spring constant of the holding section 522 is $k_v$, and the air spring constant is $k_{air}$.

In the variable wavelength interference filter 5 configured based on such a condition, when displacing the movable section 521, the air existing in the inter-reflecting film gap G1 moves to the releasing space 57 until the vibration of the movable section 521 stops. Therefore, the air spring force vanishes until the vibration of the movable section 521 stops, and the problem that the gap amount variation of the inter-reflecting film gap G1 occurs after the vibration has stopped to thereby cause mode B can be prevented. Therefore, in the variable wavelength interference filter 5 according to the present embodiment, the gap amount stabilization time from the time of applying the voltage to the electrostatic actuator 56 to the time of making a transition to the stable state in which the light with the target wavelength can be taken out can be reduced. Therefore, prompt light intensity detection by the colorimetric sensor 3, and prompt colorimetric process by the colorimetric device 1 can be performed. Further, compared to the case of making the filter internal space 58 a vacuum, the manufacturing cost can be reduced, and the production efficiency can also be improved.

Further, in the variable wavelength interference filter 5 according to the present embodiment, the electrode arrangement groove 511 is provided to the stationary substrate 51, the reflecting film installation section 512 is disposed so as to project from the electrode arrangement groove 511 toward the movable substrate 52, and the stationary reflecting film 54 is provided to the reflecting film installation section 512. Therefore, the gap amount between the electrode installation surface 511A and the movable substrate 52 in the releasing space 57 is larger than the gap amount of the inter-reflecting film gap G1, and thus there is obtained the structure in which the air in the inter-reflecting film gap G1 easily escapes to the releasing space 57 when reducing the gap amount of the inter-reflecting film gap G1. Therefore, it is possible to surely and more promptly let the air in the inter-reflecting film gap G1 out to the releasing space 57 when varying the gap amount of the inter-reflecting film gap G1, and thus, it is possible to more surely reduce the air spring force due to the air in the inter-reflecting film gap G1 acting on the movable section 521.

In the variable wavelength interference filter 5 according to the present embodiment, the movable substrate 52 is provided with the movable section 521 provided with the movable reflecting film 55, and the holding section 522 shaped like a diaphragm for holding the movable section 521 so as to be able to move back and forth with respect to the stationary substrate 51. According to such a configuration, it becomes possible to change the gap amount of the inter-reflecting film gap G1 while keeping the shape of the movable section 521 by deflecting the holding section 522, and thus, the degradation in resolution in the variable wavelength interference filter 5 can be prevented.

Further, in the variable wavelength interference filter 5 according to the present embodiment, the gap amount of the inter-reflecting film gap G1 is varied using the electrostatic actuator 56 provided with the stationary electrode 561 and the movable electrode 562. According to such a configuration, the gap amount of the inter-reflecting film gap G1 can easily be set to the desired value by applying a voltage.

Further, in the present embodiment, the variable wavelength interference filter 5 is housed in the housing 610, and is incorporated in the colorimetric sensor 3 as the optical filter device 600. Therefore, it is possible to protect the variable wavelength interference filter 5 from an external impact, and further it is possible to avoid the problem that floating substances such as charged substances adhere to the stationary reflecting film 54 and the movable reflecting film 55.

Further, in the optical filter device 600, the internal space 630 of the housing 610 is an enclosed space, and the filter internal space 58 of the variable wavelength interference filter 5 and the internal space 630 communicate with each other by way of the electrode extraction grooves 511B as the communication section. Further, by reducing the internal pressure of the housing 610 to $P_0$, the pressure of the filter internal space 58 is also set to $P_0$. According to such a configuration, by reducing the internal pressure of the housing 610, it is possible to easily set the pressure of the filter internal space 58 to the value satisfying the condition of Formula (1) described above.

It should be noted that although in the present embodiment there is shown an example of forming the communication section according to an aspect of the invention with the electrode extraction grooves 511B, it is also possible to adopt the configuration provided with, for example, the beam-like holding sections arranged at regular angular intervals centered on the planar center point O as described above, and in this case, it is possible to use the spaces between the beam-like holding sections as the communication section according to an aspect of the invention.

Second Embodiment

Next, a second embodiment of the invention will be explained with reference to the accompanying drawings.

In the first embodiment, there is adopted the configuration in which the filter internal space 58 of the variable wavelength interference filter 5 and the internal space 630 of the housing 610 communicate with each other by way of the electrode extraction grooves 511B, and the pressure of the internal space 630 of the housing 610 is reduced to the pressure $P_0$ satisfying Formula (1). In contrast thereto, the second embodiment is different from the first embodiment in the point that the filter internal space of the variable wavelength interference filter is an enclosed space having an internal pressure reduced to $P_0$.

Figure 11:
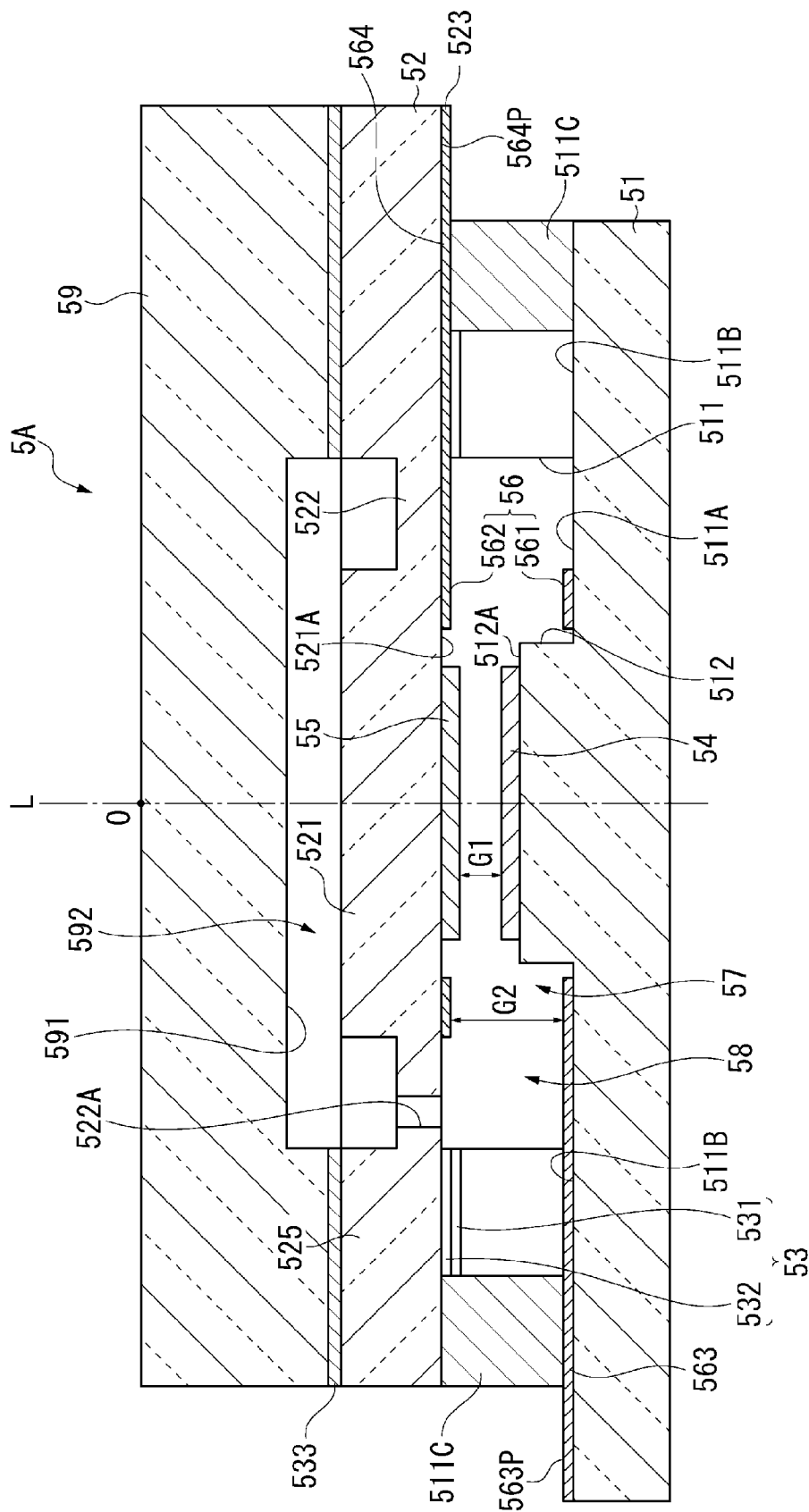
FIG. 11 is a cross-sectional view showing a schematic configuration of a variable wavelength interference filter according to a second embodiment.

FIG. 11 is a cross-sectional view showing a schematic configuration of the variable wavelength interference filter 5A according to the second embodiment. It should be noted that the constituents substantially the same as those of the first embodiment described above are denoted by the same reference symbols, and the explanation therefor will be omitted or simplified.

As shown in FIG. 11, in the variable wavelength interference filter 5A according to the present embodiment, a sealing member 511C is provided to each of the electrode extraction grooves 511B for making the filter internal space and the external space of the variable wavelength interference filter 5A communicate with each other. Due to the sealing member 511C, the filter internal space 58 is kept airtight in the present embodiment.

Further, the variable wavelength interference filter 5A has a third substrate 59 bonded to the opposite surface of the movable substrate 52 to the surface thereof to which the stationary substrate 51 is bonded.

On the surface of the third substrate 59 opposed to the movable substrate 52, there is disposed a recessed section 591 in an area overlapping the movable section 521 and the holding section 522 in the filter plan view to thereby provide a pressure holding space 592 between the bottom of the recessed section 591 and the movable substrate 52. Further, the third substrate 59 and the movable substrate 52 are tightly bonded to each other with a third bonding film 533, and the pressure holding space 592 is kept in the airtight state. As the third bonding film 533, similarly to the bonding film 53, there can be adopted a configuration of, for example, bonding a bonding film provided to the movable substrate 52 and a bonding film provided to the third substrate 59 to each other with siloxane bond or the like, and any other bonding method can also be adopted provided the configuration thereof can keep the airtightness of the pressure holding space 592.

Further, the holding section 522 of the variable wavelength interference filter 5A is provided with a communication hole 522A for making the filter internal space 58 and the pressure holding space 592 communicate with each other. Thus, when displacing the movable section 521, the pressure of the filter internal space 58 and the pressure holding space 592 are kept constant.

Here, in the variable wavelength interference filter 5A according to the present embodiment, the pressure of the filter internal space 58 and the pressure holding space 592 are kept at the pressure $P_0$ satisfying Formula (1). Thus, similarly to the first embodiment described above, when applying a voltage to the electrostatic actuator 56 to thereby displace the movable section 521, the occurrence of mode B is prevented or suppressed, and the movable section 521 vibrates in the vibration state of mode A. In other words, the gap amount of the inter-reflecting film gap G1 does not vary after the vibration of the movable section 521 has converged.

Action and Advantages of Second Embodiment

The variable wavelength interference filter 5A according to the second embodiment described above has the filter internal space 58 kept airtight, and the pressure thereof is reduced to $P_0$ satisfying Formula (1) described above. Therefore, similarly to the first embodiment described above, when displacing the movable section 521, the movable section 521 vibrates in mode A, the occurrence of mode B is prevented or suppressed, and thus it is possible to shorten the gap amount stabilization time.

It should be noted that the variable wavelength interference filter 5A according to the second embodiment can also be used as the optical filter device 600 by being housed in the housing 610 of the first embodiment, or can also be incorporated in an optical module such as the colorimetric sensor 3 by itself. Further, in the case of using it as the optical filter device 600, it is not required to reduce the internal pressure of the housing 610, and therefore, the production efficiency of the optical filter device 600 can be improved.

Modified Examples

It should be noted that the invention is not limited to the embodiments described above, but includes modifications, improvements, and so on within a range where the advantages of the invention can be achieved.

For example, although in the second embodiment the variable wavelength interference filter 5A having the pressure of the filter internal space 58 set to $P_0$ is exemplified, the invention is not limited thereto.

In the case in which, for example, the spring constant $k_v$ of the holding section 522 (the movable substrate 52) is sufficiently high, and the condition of Formula (1) is satisfied in the measurement environment such as an atmospheric pressure environment, it is also possible to use such a variable wavelength interference filter 5 as shown in FIGS. 2 and 3 directly without being housed in the housing 610. It should be noted that in this case, since the rigidity of the holding section 522 is high, the electrical power necessary for the electrostatic actuator 56 to make the deflection of the holding section 522 also increases. In this case, a configuration capable of displacing the movable section 521 with a stronger drive force can be used as the gap amount changing section according to an aspect of the invention.

Further, although in the first and second embodiments described above the configuration of providing the movable substrate 52 as the second substrate with the movable section 521 and the holding section 522 is exemplified, the invention is not limited thereto. It is also possible to adopt the configuration in which, for example, the movable substrate 52 is not provided with the holding section 522, and the gap amount of the inter-reflecting film gap G1 can be changed by causing a deflection toward the stationary substrate 51 in the entire movable substrate 52. In this case it is also possible to dispose, for example, a light transmissive reinforcing layer at the position overlapping the movable reflecting film 55 in order to prevent or suppress the deflection of the area provided with the movable reflecting film 55.

Further, although in the first and second embodiments described above there is adopted a configuration of forming the reflecting film installation section 512 projecting from the electrode arrangement groove 511 toward the movable substrate 52 to thereby make the distance between the stationary substrate 51 and the movable substrate 52 in the releasing space 57 larger than the gap amount of the inter-reflecting film gap G1, the invention is not limited thereto. It is also possible to adopt the configuration in which, for example, the reflecting film installation section 512 is not provided, and the stationary reflecting film 54 is disposed on the electrode installation surface 511A. Also in this case, the distance between the holding section 522 and the stationary substrate 51 becomes larger than the gap amount of the inter-reflecting film gap G1 due to the movable section 521 deflecting toward the stationary substrate 51, and thus it is possible to let the air existing in the inter-reflecting film gap G1 out to the releasing space 57.

Further, although in the embodiments described above the electrostatic actuator 56 is exemplified as the gap amount changing section for displacing the movable section 521 toward the stationary substrate 51, the invention is not limited thereto.

It is also possible to adopt a configuration of, for example, using a dielectric actuator disposing a first dielectric coil instead of the stationary electrode 561, and disposing a second dielectric coil or a permanent magnet instead of the movable electrode 562.

Further, it is also possible to adopt a configuration of using a piezoelectric actuator instead of the electrostatic actuator 56. In this case, for example, a lower electrode layer, a piezoelectric film, and an upper electrode layer are disposed on the holding section 522 in a stacked manner, and the voltage applied between the lower electrode layer and the upper electrode layer is varied as an input value, and thus the piezoelectric film is expanded or contracted to thereby make it possible to deflect the holding section 522.

Although the colorimetric device 1 is cited as an example of the electronic apparatus according to an aspect of the invention, the variable wavelength interference filter, the optical module, and the electronic apparatus according to an aspect of the invention can be used in a variety of fields besides the above.

For example, they can be used as an optical base system for detecting presence of a specific substance. As such a system, there can be cited, for example, an in-car gas leak detector adopting a spectroscopic measurement method using the variable wavelength interference filter according to an aspect of the invention and detecting a specific gas with high sensitivity, and a gas detection device such as an optoacoustic noble-gas detector for breath-testing.

An example of such a gas detection device will hereinafter be explained with reference to the accompanying drawings.

Figure 12:
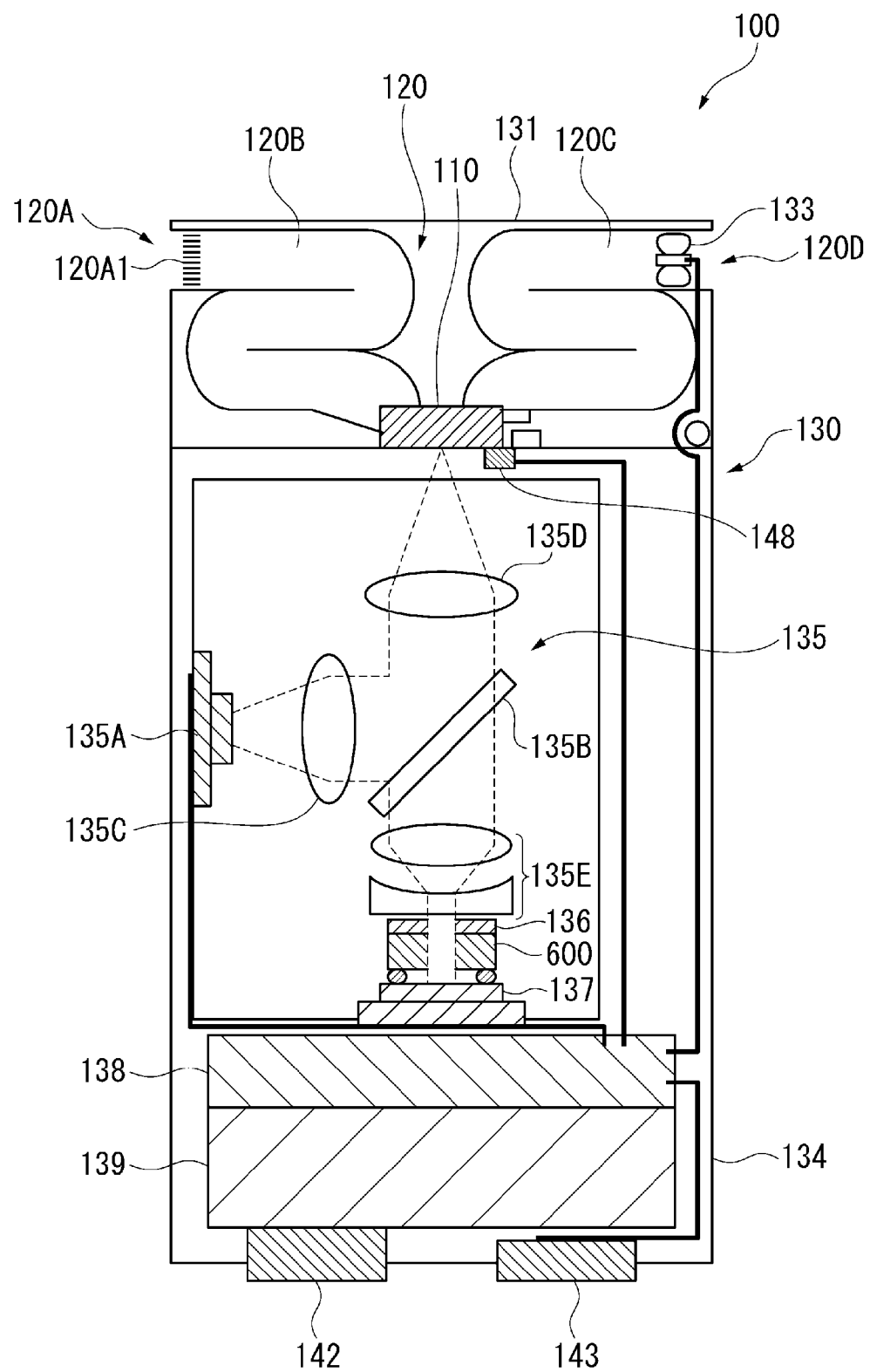
FIG. 12 is a schematic diagram showing a gas detection device provided with the variable wavelength interference filter according to an embodiment of the invention.

FIG. 12 is a schematic diagram showing an example of a gas detection device provided with the variable wavelength interference filter.

Figure 13:
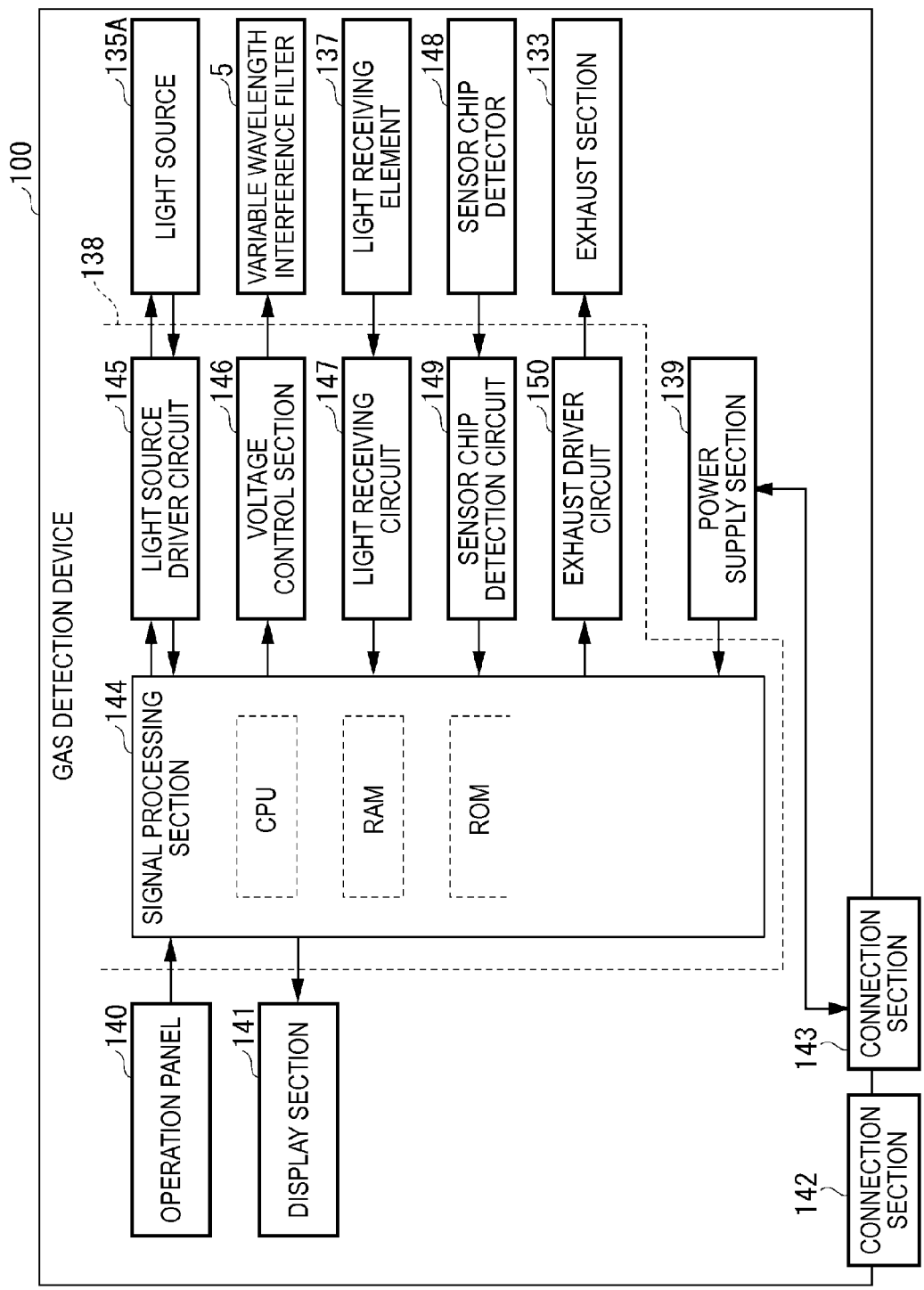
FIG. 13 is a block diagram showing a configuration of a control system of the gas detection device shown in FIG. 12.

FIG. 13 is a block diagram showing a configuration of the control system of the gas detection device shown in FIG. 12.

As shown in FIG. 12, the gas detection device 100 is configured including a sensor chip 110, a channel 120 provided with a suction port 120A, a suction channel 120B, an exhaust channel 120C, and an exhaust port 120D, and a main body section 130.

The main body section 130 is composed of a detection device (an optical module) including a sensor section cover 131 having an opening to which the channel 120 is detachably attached, an exhaust section 133, a housing 134, an optical section 135, a filter 136, the optical filter device 600, a light receiving element 137 (a detection section), and so on, a control section 138 for processing the signal thus detected and controlling the detection section, a power supply section 139 for supplying electrical power, and so on. Further, the optical section 135 is composed of a light source 135A for emitting light, a beam splitter 135B for reflecting the light, which is input from the light source 135A, toward the sensor chip 110, and transmitting the light, which is input from the sensor chip, toward the light receiving element 137, and lenses 135C, 135D, and 135E. It should be noted that although the configuration of using the optical filter device 600 provided with the variable wavelength interference filter 5 is described as an example, it is also possible to adopt a configuration of using the variable wavelength interference filter 5A described as the second embodiment. Further, it is also possible to adopt a configuration of using the optical filter device 600 incorporating such a variable wavelength interference filter 5A as described above.

Further, as shown in FIG. 13, on the surface of the gas detection device 100, there are disposed an operation panel 140, a display section 141, a connection section 142 for an interface with the outside, and a power supply section 139. In the case in which the power supply section 139 is a secondary cell, a connection section 143 for the battery charge can also be provided.

Further, as shown in FIG. 13, the control section 138 of the gas detection device 100 is provided with a signal processing section 144 composed of a CPU and so on, a light source driver circuit 145 for controlling the light source 135A, a voltage control section 146 for controlling the variable wavelength interference filter 5, a light receiving circuit 147 for receiving the signal from the light receiving element 137, a sensor chip detection circuit 149 for receiving the signal from a sensor chip detector 148 for reading a code of a sensor chip 110 and detecting presence or absence of the sensor chip 110, an exhaust driver circuit 150 for controlling the exhaust section 133, and so on.

Then, an operation of the gas detection device 100 described above will hereinafter be explained.

The sensor chip detector 148 is disposed in the sensor section cover 131 in the upper part of the main body section 130, and the sensor chip detector 148 detects presence or absence of the sensor chip 110. When detecting the detection signal from the sensor chip detector 148, the signal processing section 144 determines that it is a condition in which the sensor chip 110 is attached, and outputs a display signal for displaying that the detection operation can be performed to the display section 141.

Then, if, for example, the user operates the operation panel 140, and the operation panel 140 outputs an instruction signal indicating that the detection process will be started to the signal processing section 144, the signal processing section 144 firstly outputs the signal for operating the light source to the light source driver circuit 145 to operate the light source 135A. When the light source 135A is driven, the light source 135A emits a stable laser beam, which has a single wavelength and is a linearly polarized light. Further, the light source 135A incorporates a temperature sensor and a light intensity sensor, and the information thereof is output to the signal processing section 144. Then, if the signal processing section 144 determines that the light source 135A is operating stably based on the temperature and the light intensity input from the light source 135A, the signal processing section 144 controls the exhaust driver circuit 150 to operate the exhaust section 133. Thus, the gaseous sample including the target material (the gas molecule) to be detected is guided from the suction port 120A to the suction channel 120B, the inside of the sensor chip 110, the exhaust channel 120C, and the exhaust port 120D. It should be noted that the suction port 120A is provided with a dust filter 120A1, and relatively large dust, some water vapor, and so on are removed.

Further, the sensor chip 110 is a sensor incorporating a plurality of sets of metal nano-structures, and using localized surface plasmon resonance. In such a sensor chip 110, an enhanced electric field is formed between the metal nano-structures due to the laser beam, and when the gas molecules enter the enhanced electric field, the Raman scattered light including the information of the molecular vibration and the Rayleigh scattered light are generated.

The Rayleigh scattered light and the Raman scattered light pass through the optical section 135 and then enter the filter 136, and the Rayleigh scattered light is separated by the filter 136, and the Raman scattered light enters the variable wavelength interference filter 5 of the optical filter device 600. Then, the signal processing section 144 controls the voltage control section 146 to control the voltage to be applied to the variable wavelength interference filter 5 to thereby make the variable wavelength interference filter 5 disperse the Raman scattered light corresponding to the gas molecules to be the detection object. After then, if the light thus dispersed is received by the light receiving element 137, the light reception signal corresponding to the received light intensity is output to the signal processing section 144 by way of the light receiving circuit 147.

The signal processing section 144 compares the spectrum data of the Raman scattered light corresponding to the gas molecule to be the detection object obtained as described above and the data stored in the ROM with each other to thereby determine whether or not it is the target gas molecule, and thus the substance is identified. Further, the signal processing section 144 makes the display section 141 display the result information, or outputs it from the connection section 142 to the outside.

It should be noted that although in FIGS. 12 and 13 the gas detection device 100 for dispersing the Raman scattered light with the variable wavelength interference filter 5, and performing the gas detection based on the Raman scattered light thus dispersed is cited as an example, it is also possible to use it as a gas detection device for identifying the gas type by detecting the absorbance unique to the gas. In this case, the gas is made to flow into the sensor, and the gas sensor for detecting the light absorbed by the gas in the incident light is used as the optical module according to an aspect of the invention. Further, the gas detection device for analyzing and determining the gas flowing into the sensor with such a gas sensor is cited as the electronic apparatus according to an aspect of the invention. It is possible to detect the component of the gas using the variable wavelength interference filter according to an aspect of the invention also in such a configuration.

Further, as the system for detecting the presence of the specific substance, besides the gas detection described above, there can be cited a substance component analysis device such as a non-invasive measurement device of sugar group using near-infrared dispersion or a non-invasive measurement device of the information of food, biological object, or mineral.

Hereinafter, as an example of the substance component analysis device described above, a food analysis device will be explained.

Figure 14:
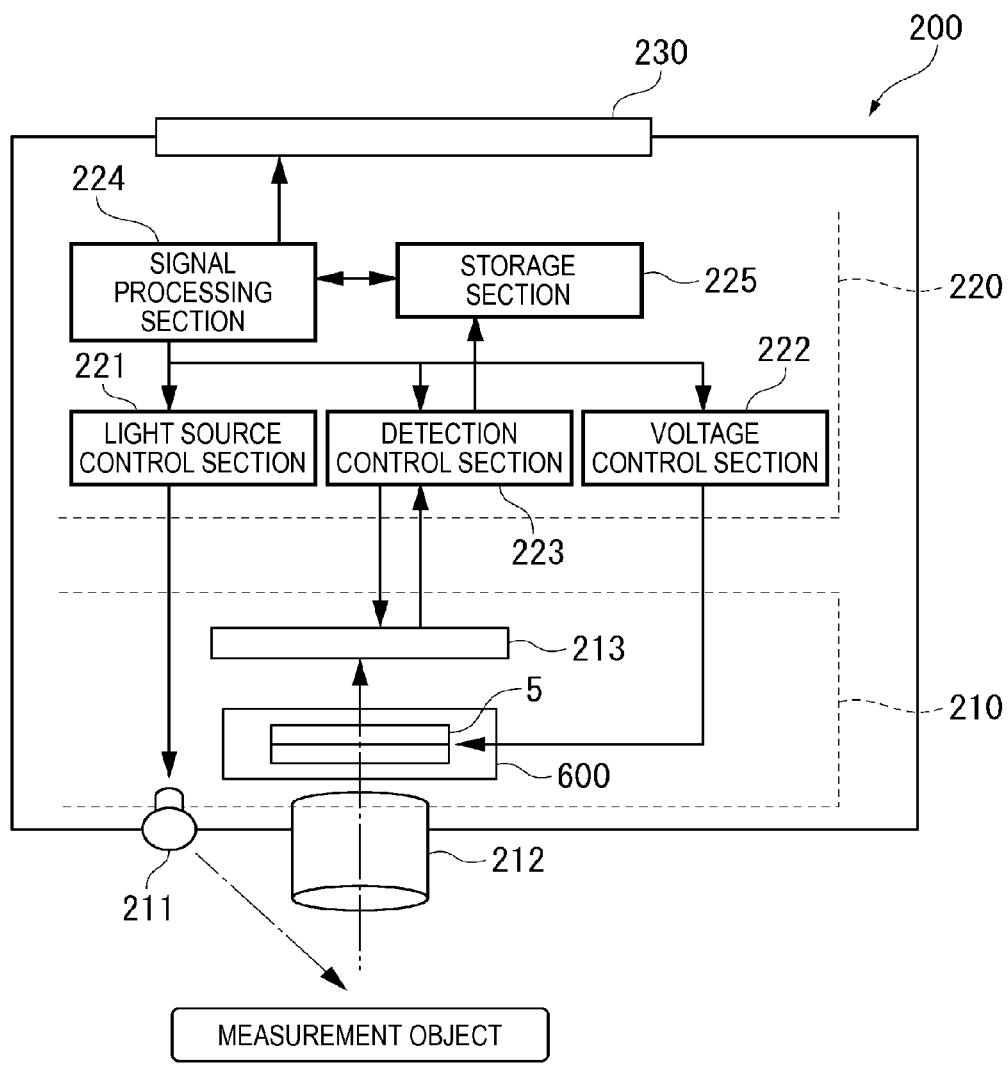
FIG. 14 is a diagram showing a schematic configuration of a food analysis device provided with the variable wavelength interference filter according to an embodiment of the invention.

FIG. 14 is a diagram showing a schematic configuration of the food analysis device as an example of the electronic apparatus using the variable wavelength interference filter 5. It should be noted that although an example in which the optical filter device 600 provided with the variable wavelength interference filter 5 is disposed is described here, it is also possible to adopt the configuration in which the variable wavelength interference filter 5A according to the second embodiment is directly disposed.

As shown in FIG. 14, the food analysis device 200 is provided with a detector 210 (the optical module), a control section 220, and a display section 230. The detector 210 is provided with a light source 211 for emitting light, an image pickup lens 212 to which the light from a measurement object is introduced, the optical filter device 600 provided with the variable wavelength interference filter 5 for dispersing the light thus introduced from the image pickup lens 212, and an image pickup section 213 (a detection section) for detecting the light thus dispersed.

Further, the control section 220 is provided with a light source control section 221 for performing lighting and extinction control of the light source 211 and brightness control when lighting, a voltage control section 222 for controlling the variable wavelength interference filter 5, a detection control section 223 for controlling the image pickup section 213 and obtaining a spectral image picked up by the image pickup section 213, a signal processing section 224, and a storage section 225.

In the food analysis device 200, when the system is started up, the light source control section 221 controls the light source 211, and the light source 211 irradiates the measurement object with light. Then, the light reflected by the measurement object passes through the image pickup lens 212 and then enters the variable wavelength interference filter 5. The voltage with which the variable wavelength interference 5 can disperse the light into desired wavelengths is applied to the variable wavelength interference filter 5 under the control of the voltage control section 222, and the light thus dispersed is picked up by the image pickup section 213 formed of, for example, a CCD camera. Further, the light thus picked up is stored in the storage section 225 as the spectral image. Further, the signal processing section 224 controls the voltage control section 222 to vary the voltage value to be applied to the variable wavelength interference filter 5 to thereby obtain the spectral image corresponding to each wavelength.

Then, the signal processing section 224 performs an arithmetic process on the data of each pixel in each of the images stored in the storage section 225 to thereby obtain the spectrum in each pixel. Further, the storage section 225 stores, for example, information related to component of food corresponding to the spectrum, and the signal processing section 224 analyzes the data of the spectrum thus obtained based on the information related to the food stored in the storage section 225, and then obtains the food component included in the detection object and the content thereof. Further, the calorie of the food, the freshness thereof, and so on can also be calculated based on the food component and the content thus obtained. Further, by analyzing the spectral distribution in the image, it is possible to perform extraction of the portion with low freshness in the food as a test object, and further, it is also possible to perform detection of a foreign matter included in the food.

Then, the signal processing section 224 performs a process of making the display section 230 display the information of the components, the contents, the calorie, the freshness, and so on of the food as the test object obtained as described above.

Further, in FIG. 14, an example of the food analysis device 200 is shown. It is also possible to use substantially the same configuration as the non-invasive measurement device of other information as described above. For example, it can be used as a biological analysis device for analyzing a biological component such as measurement and analysis of a biological fluid such as blood. If as such a biological analysis device, for example, a device of detecting ethyl alcohol is provided as a device of measuring the biological fluid component such as blood, the device can be used as a device for detecting the influence of alcohol to the driver to thereby prevent driving under the influence of alcohol. Further, it can also be used as an electronic endoscopic system equipped with such a biological analysis device.

Further, it can also be used as a mineral analysis device for performing component analysis of minerals.

Further, the variable wavelength interference filter, the optical module, and the electronic apparatus according to an aspect of the invention can be applied to the following devices.

For example, it is also possible to transmit data with the light having each of the wavelengths by temporally varying the intensity of the light having each of the wavelengths, and in this case, it is possible to extract the data transmitted with the light having a specific wavelength by dispersing the light having the specific wavelength using the variable wavelength interference filter provided to the optical module, and then making the light receiving section receive the light. Therefore, by processing the data of the light having each of the wavelengths using the electronic apparatus equipped with such a data extracting optical module, it is also possible to perform optical communication.

Further, the electronic apparatus can be applied to a spectroscopic camera for picking up the spectral image and a spectroscopic analysis device by dispersing the light with the variable wavelength interference filter according to an aspect of the invention. As an example of such a spectroscopic camera, an infrared camera incorporating the variable wavelength interference filter can be cited.

Figure 15:
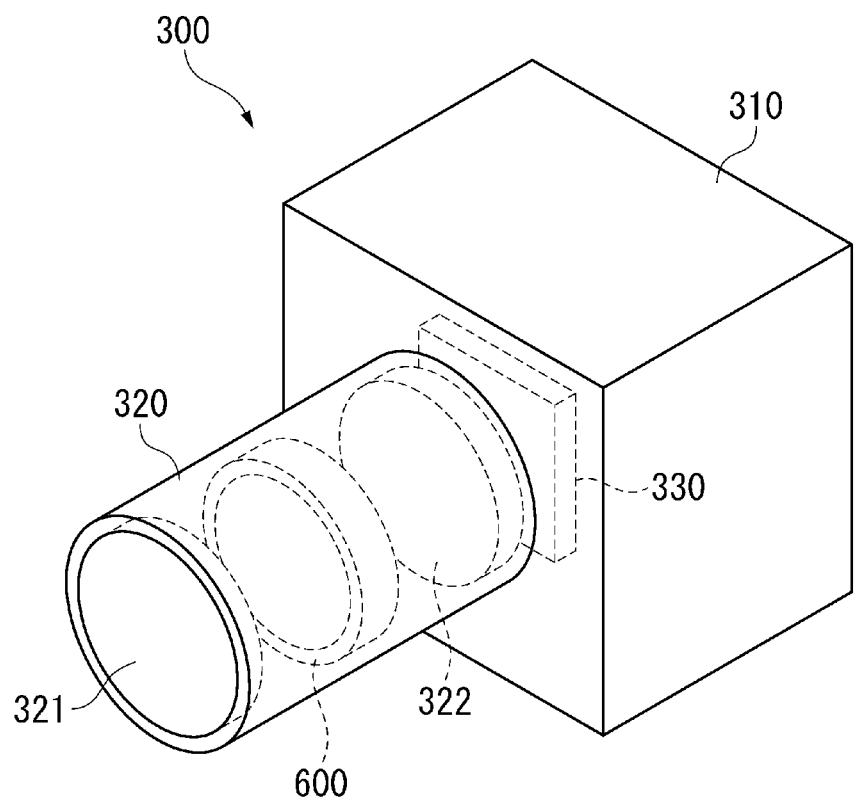
FIG. 15 is a schematic diagram showing a schematic configuration of a spectroscopic camera provided with the variable wavelength interference filter according to an embodiment of the invention.

FIG. 15 is a schematic diagram showing a schematic configuration of the spectroscopic camera. As shown in FIG. 15, the spectroscopic camera 300 is provided with a camera main body 310, an image pickup lens unit 320, and an image pickup section 330 (a detection section).

The camera main boy 310 is a part which is gripped and operated by the user.

The image pickup lens unit 320 is provided to the camera main body 310, and guides the image light input thereto to the image pickup section 330. Further, as shown in FIG. 15, the image pickup lens unit 320 is configured including an objective lens 321, an imaging lens 322, and the optical filter device 600 having the variable wavelength interference filter 5 disposed between these lenses.

The image pickup section 330 is formed of a light receiving element, and picks up the image light guided by the image pickup lens unit 320.

In such a spectroscopic camera 300, by transmitting the light with the wavelength to be the imaging object using the variable wavelength interference filter 5, the spectral image of the light with a desired wavelength can be picked up.

Further, the variable wavelength interference filter can be used as a band-pass filter, and can also be used as, for example, an optical laser device for dispersing and transmitting only the light with a narrow band centered on a predetermined wavelength out of the light in a predetermined wavelength band emitted by the light emitting element using the variable wavelength interference filter.

Further, the variable wavelength interference filter can be used as a biometric authentication device, and can be applied to, for example, an authentication device of blood vessels, a fingerprint, a retina, an iris, and so on using the light in a near infrared range or a visible range.

Further, the optical module and the electronic apparatus can be used as a concentration detection device. In this case, the infrared energy (the infrared light) emitted from the substance is dispersed by the variable wavelength interference filter and is then analyzed, and the concentration of the test object in a sample is measured.

As described above, the variable wavelength interference filter, the optical module, and the electronic apparatus according to an aspect of the invention can be applied to any device for dispersing predetermined light from the incident light. Further, since the variable wavelength interference filter according to an aspect of the invention can disperse the light into a plurality of wavelengths with a single device as described above, the measurement of the spectrum of a plurality of wavelengths and detection of a plurality of components can be performed with accuracy. Therefore, compared to the conventional device of taking out desired wavelengths with a plurality of devices, downsizing of the optical module and the electronic apparatus can be promoted, and the optical module and the electronic apparatus can preferably be used as, for example, the portable or in-car optical device.

Besides the above, specific structures to be adopted when putting the invention into practice can arbitrarily be replaced with other structures and so on within the range in which the advantages of the invention can be achieved.

The entire disclosure of Japanese Patent Application No. 2011-214876, filed Sep. 29, 2011 is expressly incorporated by reference herein.

What is claimed is:

1. A variable wavelength interference filter comprising:
a first substrate;
a second substrate opposed to the first substrate, the second substrate being bonded to the first substrate;
a first reflecting film provided to the first substrate;
a second reflecting film provided to the second substrate, the second reflecting film being opposed to the first reflecting film across an inter-reflecting film gap having a predetermined gap amount; and
a gap amount changing section adapted to vary the gap amount of the inter-reflecting film gap by moving the second substrate relative to the first substrate,
wherein a releasing space, to which gas between the first reflecting film and the second reflecting film moves when the second substrate moves closer to the first substrate due to the gap amount changing section, is provided between the first substrate and the second substrate, the releasing space being in communication with an exterior of the filter through an extraction electrode groove formed in the first substrate that extends outward from the releasing space, and
an air spring constant of the gas between the first reflecting film and the second reflecting film is $k_{air}$, and a spring constant of the second substrate is $k_v$, the following relationship is satisfied:

$$k_v \geq 20 \times k_{air}.$$

2. The variable wavelength interference filter according to claim 1, wherein
a distance between the first substrate and the second substrate across the releasing space is larger than the gap amount of the inter-reflecting film gap.

3. The variable wavelength interference filter according to claim 1, wherein
the second substrate includes:
a movable section provided with the second reflecting film, and
a holding section adapted to support the movable section such that the holding section is movable back and forth with respect to the first substrate.

4. The variable wavelength interference filter according to claim 1, wherein
the gap amount changing section includes:
a first electrode provided to the first substrate, and
a second electrode provided to the second substrate, the second electrode being opposed to the first electrode across an inter-electrode gap.

5. A variable wavelength interference filter comprising:
a first substrate;
a first reflecting film provided on the first substrate;
a second reflecting film provided to a second substrate, the second reflecting film being opposed to the first reflecting film via a gap; and
a distance changing section adapted to change a distance of the gap between the first reflecting film and the second reflecting film by moving the second substrate,
wherein the gap is in communication with an exterior of the filter through an extraction electrode groove formed in the first substrate that extends outward from the gap; and
wherein an air spring constant of the gas between the first reflecting film and the second reflecting film is $k_{air}$, and a spring constant of the second substrate is $k_v$, the following relationship is satisfied:

$$k_v \geq 20 \times k_{air}.$$

6. An optical filter device comprising:
a variable wavelength interference filter including:
a first substrate,
a second substrate opposed to the first substrate, the second substrate being bonded to the first substrate,
a first reflecting film provided to the first substrate,
a second reflecting film provided to the second substrate, the second reflecting film being opposed to the first reflecting film across an inter-reflecting film gap having a predetermined gap amount, and
a gap amount changing section adapted to vary the gap amount of the inter-reflecting film gap by moving the second substrate relative to the first substrate,
wherein a releasing space, to which gas between the first reflecting film and the second reflecting film moves when the second substrate moves closer to the first substrate due to the gap amount changing section, is provided between the first substrate and the second substrate;
the releasing space is in communication with an exterior of the filter through a communication section formed in the first substrate that extends outward from the releasing space, and
a housing adapted to house the variable wavelength interference filter,
wherein the housing has an enclosed structure, and has an internal pressure set to a state satisfying the following relationship $$k_v \geq 20 \times k_{air}, \text{ and}$$

the communication section communicably interconnects the releasing space with an internal space of the housing, and the communication section is sandwiched between the first substrate and the second substrate,
wherein an air spring constant of the gas between the first reflecting film and the second reflecting film is $k_{air}$, and a spring constant of the second substrate is $k_v$, the following relationship is satisfied:

$$k_v \geq 20 \times k_{air}.$$

7. An optical filter device comprising:
a first substrate;
a first reflecting film provided on the first substrate;
a second reflecting film provided to a second substrate, the second reflecting film being opposed to the first reflecting film via a gap; and
a distance changing section adapted to change a distance of the gap between the first reflecting film and the second reflecting film by moving the second substrate, wherein the gap is in communication with an exterior of the device through an extraction electrode groove formed in the first substrate that extends outward from the gap; and a housing adapted to house the first substrate, the first reflecting film, the second substrate, the second reflecting film, and the distance changing section, wherein an air spring constant of the gas between the first reflecting film and the second reflecting film is $k_{air}$, and a spring constant of the second substrate is $k_v$, the following relationship is satisfied:

$k_v \geq 20 \times k_{air}$.

8. An optical module comprising:
a first substrate;
a second substrate opposed to the first substrate, the second substrate being bonded to the first substrate;
a first reflecting film provided to the first substrate;
a second reflecting film provided to the second substrate, and the second reflecting film being opposed to the first reflecting film across an inter-reflecting film gap having a predetermined gap amount;
a gap amount changing section adapted to vary the gap amount of the inter-reflecting film gap by moving the second substrate relative to the first substrate; and
a detection section adapted to detect light emitted by the first reflecting film and the second reflecting film,
wherein a releasing space, to which gas between the first reflecting film and the second reflecting film moves when the second substrate moves closer to the first substrate due to the gap amount changing section, is provided between the first substrate and the second substrate, the releasing space being in communication with an exterior of the module through an extraction electrode groove formed in the first substrate that extends outward from the releasing space, and
an air spring constant of the gas between the first reflecting film and the second reflecting film is $k_{air}$, and a spring constant of the second substrate is $k_v$, the following relationship is satisfied:

$k_v \geq 20 \times k_{air}$.

9. An optical module comprising:
a first substrate;
a first reflecting film provided on the first substrate;
a second reflecting film provided to a second substrate, the second reflecting film being opposed to the first reflecting film via a gap; and
a distance changing section adapted to change a distance of the gap between the first reflecting film and the second reflecting film by moving the second substrate;
wherein the gap is in communication with an exterior of the device through an extraction electrode groove formed in the first substrate that extends outward from the gap; and a detection section adapted to detect light emitted by the first reflecting film and the second reflecting film,
wherein an air spring constant of the gas between the first reflecting film and the second reflecting film is $k_{air}$, and a spring constant of the second substrate is $k_v$, the following relationship is satisfied:

$k_v \geq 20 \times k_{air}$.

10. An electronic apparatus comprising:
a first substrate;
a second substrate opposed to the first substrate, the second substrate being bonded to the first substrate;
a first reflecting film provided to the first substrate;
a second reflecting film provided to the second substrate, the second reflecting film being opposed to the first reflecting film across an inter-reflecting film gap having a predetermined gap amount; and
a gap amount changing section adapted to vary the gap amount of the inter-reflecting film gap by moving the second substrate relative to the first substrate,
wherein a releasing space, to which gas between the first reflecting film and the second reflecting film moves when the second substrate moves closer to the first substrate due to the gap amount changing section, is provided between the first substrate and the second substrate, the releasing space being in communication with an exterior of the apparatus through an extraction electrode groove formed in the first substrate that extends outward from the releasing space, and
an air spring constant of the gas between the first reflecting film and the second reflecting film is $k_{air}$, and a spring constant of the second substrate is $k_v$, the following relationship is satisfied:

$k_v \geq 20 \times k_{air}$.

11. An electronic apparatus comprising:
a first substrate;
a first reflecting film provided on the first substrate;
a second reflecting film provided to a second substrate, the second reflecting film being opposed to the first reflecting film via a gap; and
a distance changing section adapted to change a distance of the gap between the first reflecting film and the second reflecting film by moving the second substrate;
wherein the gap is in communication with an exterior of the apparatus through an extraction electrode groove formed in the first substrate that extends outward from the gap; and
wherein an air spring constant of the gas between the first reflecting film and the second reflecting film is $k_{air}$, and a spring constant of the second substrate is $k_v$, the following relationship is satisfied:

$k_v \geq 20 \times k_{air}$.

* * * * *